United States Patent [19]

Lang

[11] Patent Number: 4,965,260

[45] Date of Patent: Oct. 23, 1990

[54] BICYCLIC BETA-LACTAM CARBOXYLIC ACIDS

[75] Inventor: Marc Lang, Rixheim, France

[73] Assignee: Ciba-Geigy Corporation, Ardsley, N.Y.

[21] Appl. No.: 153,377

[22] Filed: Feb. 8, 1988

[30] Foreign Application Priority Data

Feb. 11, 1987 [CH] Switzerland ............................ 498/87
Sep. 3, 1987 [CH] Switzerland ........................... 3373/87

[51] Int. Cl.$^5$ .................. C07D 499/00; A61K 31/425
[52] U.S. Cl. ..................................... 514/192; 514/195; 540/310
[58] Field of Search ................ 540/310; 514/192, 193, 514/195

[56] References Cited

U.S. PATENT DOCUMENTS

| 4,272,437 | 6/1981 | Menard et al. ................. 260/239 A |
| 4,558,042 | 12/1985 | Foglio et al. ......................... 540/310 |
| 4,692,442 | 9/1987 | Gosteli et al. ....................... 514/195 |
| 4,863,914 | 9/1989 | Perrone et al. ..................... 514/192 |
| 4,886,793 | 12/1989 | Perrone et al. ..................... 540/310 |

FOREIGN PATENT DOCUMENTS

| 070204 | 1/1983 | European Pat. Off. . |
| 170028 | 2/1986 | European Pat. Off. . |
| 236880 | 9/1987 | European Pat. Off. . |
| 2043639 | 10/1980 | United Kingdom . |
| 2104509 | 3/1983 | United Kingdom . |

OTHER PUBLICATIONS

Bruna et al., 26th ICAAC 1986 Abstract No. 1286.

Primary Examiner—Nicholas S. Rizzo
Attorney, Agent, or Firm—JoAnn Villamizar

[57] ABSTRACT

Compounds of the formula

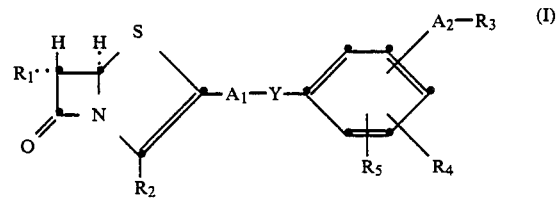

in which $R_1$ is lower alkyl substituted by hydroxy or by protected hydroxy, $R_2$ represents carboxy or functionally modified carboxy, $R_3$ is hydrogen, amino, mono- or di-substituted amino, carbamoyl, hydroxy, protected hydroxy, carbamoyloxy, lower alkoxy, halogen, lower alkanoyl, sulphamoyl or heteroarylthio, each of $R_4$ and $R_5$, independently of the other, represents hydrogen, lower alkyl, hydroxy, protected hydroxy, lower alkoxy, halogen, amino, protected amino, lower alkanoylamino or carbamoyl, or $R_4$ and $R_5$ together represent methylenedioxy, Y represents a group of the formula —O—, —S— or —$NR_6$—, $R_6$ is hydrogen or lower alkyl, $A_1$ represents lower alkylene or unsubstituted or substituted phenylene and $A_2$ represents a direct bond or lower alkylene, and salts of such compounds, have antibacterial activity. The compounds of the formula I are manufactured by processes that are known per se.

8 Claims, No Drawings

BICYCLIC BETA-LACTAM CARBOXYLIC ACIDS

The invention relates to novel bicyclic betalactam-carboxylic acids of the formula

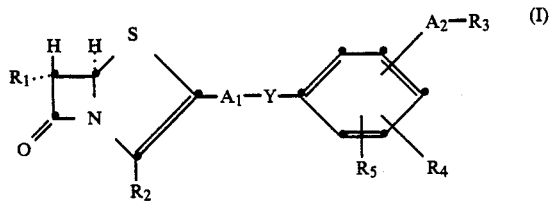

in which $R_1$ is a lower alkyl substituted by hydroxy or by protected hydroxy, $R_2$ represents carboxy or functionally modified carboxy, $R_3$ is hydrogen, aminom, mono- or di-substituted amino carbamoyl, hydroxy, protected hydroxy, carbamoyloxy, lower alkoxy, halogen, lower alkanoyl, sulphamoyl or heteroarylthio, each of $R_4$ and $R_5$, independently of the other, represents hydrogen, lower alkyl, hydroxy, protected hydroxy, lower alkoxy, halogen, amino, protected amino, lower aklanoyl-amino or carbamoyl, or $R_4$ and $R_5$ together represent methylenedioxy, Y represents a group of the formula —O—, —S— or —NR$_6$—, $R_6$ is hydrogen or lower alkyl, $A_1$ represents lower alkylene or unsubstituted or substituted phenylene and $A_2$ represents a direct bond or lower alkylene, to salts of compounds of the formula I having a salt-forming group, to processes for the manufacture of compounds of the formula I, to pharmaceutical preparations that contain such compounds, and to their use for the manufacture of pharmaceutical preparations or as active ingredients in medicaments.

Within the scope of the present description, the definitions used hereinbefore and hereinafter have preferably the following meanings:

Functionally modified carboxy $R_2$ is especially esterified carboxy that is cleavable under physiological conditions or protected carboxy $R_{2'}$.

An esterified carboxy group $R_2$ that is cleavable (i.e. metabolisable) under physiological conditions is especially an acyloxymethoxycarbonyl group or, alternatively, an acylaminomethoxycarbonyl group, wherein acyl is, for example, the radical of an organic carboxylic acid, especially of an unsubstituted or, for example, amino-substituted lower alkanecarboxylic acid or arenecarboxylic acid, for example benzoic acid, or wherein acyloxymethyl forms the radical of a lactone. Such groups are, for example, lower alkanoyloxymethoxy-carbonyl, amino-lower alkanoyloxymethoxycarbonyl, especially α-amino-lower alkanoyloxymethoxycarbonyl, and lower alkanoylaminomethoxycarbonyl. Other esterified carboxy groups $R_2$ that are cleavable under physiological conditions are, for example, 3-phthalidyloxy-carbonyl, 1-lower alkoxycarbonyloxy-lower alkoxy-carbonyl, 1-lower alkoxy-lower alkoxycarbonyl or 2-oxo-1,3-dioxolen-4-ylmethoxycarbonyl which is unsubstituted or is substituted by lower alkyl or by phenyl in the 5-position of the dioxolene ring.

Mono- or di-substituted amino $R_3$ is, for example, amino mono- or di-substituted by lower alkyl, hydroxy-lower alkyl, carbamoyl-lower alkyl, optionally N-lower alkylated amino-lower alkyl, such as amino-lower alkyl, lower alkylamino-lower alkyl or di-lower alkylamino-lower alkyl, heteroaryl, heteroaryl-lower alkyl and/or by N-azaheterocyclyl-lower alkyl, or is aminomethylene-amino, guanidino, N-azaheterocyclyl or protected amino.

Heteroaryl as substituent of an amino group $R_3$, in heteroaryl-lower alkyl as substituent of an amino group $R_3$ or in heteroarylthio $R_3$ is especially a monocyclic 5- or 6-membered heteroaryl radical that has from 1 to 4 ring nitrogen atoms and is bonded by way of a ring carbon atom, such as pyrrolyl, for example 2- or 3-pyrrolyl, imidazolyl, such as 2- or 4-imidazolyl, pyrazolyl, such as 3- or 4-pyrazolyl, triazolyl, such as 1H-1,3,4-triazol-2-yl or 1H-1,2,4-triazol-3-yl, tetrazolyl, such as 1H- or 2H-tetrazol-5-yl, pyridyl, such as 2-, 3- or 4-pyridyl, or pyrimidyl, such as 2-, 4- or 5-pyrimidyl.

N-azaheterocyclyl as substituent $R_3$ or in amino $R_3$ substituted by N-azaheterocyclyl-lower alkyl is, for example, a monocyclic 5-membered heteroaryl radical that has from 1 to 4 ring nitrogen atoms and is bonded by way of an uncharged ring nitrogen atom, such as 1-pyrrolyl, 1-imidazolyl, 1-pyrazolyl, 1H-1,2,4-triazol-1-yl, 1H-1,3,4-triazol-1-yl, 1H-tetrazol-1-yl or 2H-tetrazol-2-yl, a monocyclic partially saturated 6-membered heteroaryl radical that has from 1 to 3 ring nitrogen atoms and is bonded by way of an uncharged ring nitrogen atom, such as 1,4-dihydropyrid-1-yl, or a monocyclic saturated 5- or 6-membered azaheterocyclyl radical that has from 1 to 3 ring nitrogen atoms and optionally an additional ring hetero atom selected from the group comprising sulphur and oxygen, and that is bonded by way of an uncharged ring nitrogen atom, such as pyrrolidin-1-yl, piperidin-1-yl, piperazin-1-yl, morpholin-4-yl or thiomorpholin-4-yl, and benzo derivatives thereof, for example 1,3-dihydro-isoindol-2-yl or 1,2,3,4-tetrahydro-isoquinolin-2-yl.

The mentioned heteroaryl and N-azaheterocyclyl radicals are unsubstituted or may be substituted, such as mono- or di-substituted, by hydroxy, lower alkoxy, halogen, lower alkylthio, phenylthio, lower alkyl, hydroxy-lower alkyl, lower alkanoyloxy-lower alkyl, carboxy-lower alkyl, carbamoyl-lower alkyl, carbamoyloxy-lower alkyl, halo-lower alkyl, optionally N-lower alkylated amino-lower alkyl, such as amino-lower alkyl, lower alkylamino-lower alkyl or di-lower alkylamino-lower alkyl, lower alkanoylamino-lower alkyl, sulpho-lower alkyl, lower alkanoyl, optionally substituted amino, such as amino, lower alkylamino, di-lower alkylamino or lower alkanoylamino, optionally functionally modified carboxy or sulpho, such as carboxy, lower alkoxycarbonyl, carbamoyl, cyano, sulpho or sulphamoyl, pyridyl, such as 2-, 3- or 4-pyridyl, and/or by phenyl or phenyl substituted by lower alkyl, lower alkoxy and/or by halogen, and N-azaheterocyclyl radicals having a di-substitutable ring carbon atom may also be substituted by oxo. The substituents are preferably bonded to ring carbon atoms and, in the case of saturated azaheterocyclyl radicals, also to secondary ring nitrogen atoms Lower alkyl in heteroaryl-lower alkyl and N-azaheterocyclyl-lower alkyl radicals has from 1 to 4, especially 1 or 2, carbon atoms Phenylene $A_1$ is 1,2-, 1,3- or especially 1,4-phenylene which is unsubstituted or is substituted, for example, by lower alkyl, hydroxy, lower alkoxy, amino or by halogen.

In the present description, the term "lower" used in connection with definitions of groups and compounds denotes that the groups and compounds so designated, unless expressly defined otherwise, contain from 1 to 7, preferably from 1 to 4, carbon atoms.

Lower alkyl $R_1$ substituted by hydroxy is especially lower alkyl substituted by hydroxy in the α-position with respect to the penem ring structure, and is, for example, 1-hydroxyprop-1-yl, 2-hydroxyprop-2-yl, 1-hydroxybut-1-yl and especially hydroxymethyl or 1-hydroxyethyl, whilst hydroxy-lower alkyl as substituent of the radical $R_3$ is, for example, 1-hydroxyethyl or especially 2-hydroxyethyl, and as substituent of a heteroaryl or azaheterocyclyl radical is also hydroxymethyl.

Lower alkanoyloxymethoxycarbonyl is, for example, acetoxymethoxycarbonyl or pivaloyloxymethoxycarbonyl. α-Amino-lower alkanoyloxymethoxycarbonyl is, for example, glycyloxymethoxycarbonyl, L-valyloxymethoxycarbonyl or L-leucyloxymethoxycarbonyl. Lower alkanoylaminomethoxycarbonyl is, for example, acetaminomethoxy-carbonyl. 1-Lower alkoxycarbonyloxy-lower alkoxycarbonyl is, for example, ethoxycarbonyloxymethoxycarbonyl or 1-ethoxycarbonyloxyethoxycarbonyl. 1-Lower alkoxy-lower alkoxycarbonyl is, for example, methoxymethoxycarbonyl or 1-methoxyethoxycarbonyl. A 2-oxo-1,3-dioxolen-4-ylmethoxy group that is unsubstituted or is substituted by lower alkyl or phenyl in the 5-position of the dioxolene ring is especially a 5-phenyl- and more especially a 5-methyl-2-oxo-1,3-dioxolen-4-ylmethoxy group.

Lower alkyl as the radical $R_4$, $R_5$ or $R_6$ or as substituent of a phenylene radical $A_1$ or of a radical $R_3$ is, for example, ethyl, n-propyl, isopropyl or n-butyl, but especially methyl.

Carbamoyl-lower alkyl is, for example, carbamoylmethyl or 2-carbamoylethyl.

Amino-lower alkyl is, for example, aminomethyl or 2-aminoethyl, whilst lower alkylamino-lower alkyl is, for example, methylaminomethyl, ethylaminomethyl, 2-methylaminoethyl or 2-ethylaminoethyl; di-lower alkylamino-lower alkyl is, for example, dimethylaminomethyl, 2-dimethylaminoethyl or 2-diethylaminoethyl; and lower alkanoylamino-lower alkyl is, for example, acetaminomethyl, 2-acetaminoethyl or formylaminomethyl.

Lower alkoxy is, for example, methoxy, or ethoxy, n-propoxy, isopropoxy, n-butoxy, isobutoxy or tert.-butoxy.

Halogen is, for example, chlorine, bromine and especially fluorine.

Lower alkylthio is, for example, methylthio, ethylthio or n-propylthio.

Lower alkanoyloxy-lower alkyl is, for example, acetoxymethyl or 2-acetoxyethyl.

Carboxy-lower alkyl is, for example, carboxymethyl, 1-carboxy-, 2-carboxy- or 1,2-dicarboxy-ethyl.

Carbamoyloxy-lower alkyl is, for example, carbamoyloxymethyl or 2-carbamoyloxyethyl.

Halo-lower alkyl is, for example, chloromethyl, bromomethyl, 2-chloroethyl or 2,2-dichloroethyl.

Sulpho-lower alkyl is, for example, sulphomethyl or 2-sulphoethyl.

Lower alkylamino is, for example, methylamino, ethylamino, n-propylamino, isopropylamino or n-butylamino, whilst di-lower alkylamino is, for example, dimethylamino, diethylamino, di-n-propylamino or diisopropylamino, and lower alkanoylamino is, for example, formylamino, acetylamino or propionylamino.

Lower alkoxycarbonyl is, for example, methoxycarbonyl or ethoxycarbonyl

Lower alkanoyl is, for example, formyl or acetyl.

Lower alkylene $A_1$ and $A_2$ is especially straight-chained lower alkylene having from 1 to 5 carbon atoms, for example methylene, ethylene, 1,3-propylene or 1,4-butylene, but may also be branched lower alkylene having from 2 to 5 carbon atoms, such as methylene, ethylene or 1,3-propylene each substituted by methyl, or ethylene substituted by ethyl Such branched lower alkylene radicals are, for example, ethylidene, 1,2-propylene, 1,2-butylene, 1,3-butylene or 2-methyl-1,3-butylene.

In compounds of the formula I in which $R_4$ and $R_5$ together represent methylenedioxy, the two-bonded substituent methylenedioxy is bonded to two adjacent carbon atoms, especially carbon atoms 3 and 4, of the phenyl ring.

Examples of heteroaryl as substituent of an amino group $R_3$, in heteroaryl-lower alkyl as substituent of an amino group $R_3$ or in heteroarylthio $R_3$ are unsubstituted pyridyl or pyridyl substituted by carbamoyl, such as 2-, 3- or 4-pyridyl, or unsubstituted 1H-tetrazol-5-yl or 1H-tetrazol-5-yl substituted by lower alkyl, carboxy-lower alkyl, sulpho-lower alkyl, optionally N-lower alkylated amino-lower alkyl or by carbamoyl-lower alkyl N-azaheterocyclyl as the radical $R_3$ or in amino $R_3$ substituted by Nazahetero-cyclyl-lower alkyl is, for example, unsubstituted 1-imidazolyl or 1-imidazolyl substituted by lower alkyl, unsubstituted 1H-tetrazol-1-yl or 1H-tetrazol-1-yl substituted by lower alkyl, unsubstituted 1,4-dihydropyrid-1-yl or 1,4-dihydro-pyrid-1-yl substituted by lower alkyl, hydroxy, oxo and/or by carbamoyl, pyrrolidin-1-yl, unsubstituted piperidin-1-yl or piperidin-1-yl substituted by lower alkyl, amino-lower alkyl, hydroxy-lower alkyl, hydroxy or by carbamoyl, morpholin-4-yl, thiomorpholin-4-yl, or piperazin-1-yl which is unsubstituted or is substituted by lower alkyl, carbamoyl-lower alkyl, carbamoyl, lower alkanoyl or by pyridyl Hydroxymethyl and, more especially, 1-hydroxyethyl are preferred as radicals $R_1$. Preferred esterified carboxy groups $R_2$ that are cleavable under physiological conditions are, for example, lower alkanoyloxymethoxycarbonyl, for example acetoxymethoxycarbonyl or pivaloyloxymethoxycarbonyl, and 1-lower alkoxycarbonyloxy-lower alkoxycarbonyl, for example 1-ethoxycarbonyloxyethoxycarbonyl. $R_3$ preferably represents carbamoyl, carbamoyloxy, amino, methylamino, dimethylamino, (2-hydroxyethyl)-amino, bis-(2-hydroxyethyl)-amino, (4-pyridyl)-amino, (3-pyridyl)-amino, morpholin-4-yl, piperazin-1-yl, 4-carbamoylpiperazin-1-yl, 3-hydroxy-4-oxo-1,4-dihydropyridin-1-yl, 1H-tetrazol-1-yl, pyridin-4-ylthio or 1-methyl-1H-tetrazol-5-ylthio. The preferred meaning of the radicals $R_4$ and $R_5$ is hydrogen. Y is preferably an —O— group. In preferred compounds of the formula I, $A_1$ represents lower alkylene having 1 or 2 carbon atoms and $A_2$ represents a direct bond or lower alkylene having 1 or 2 carbon atoms, the grouping —$A_2$—$R_3$ being arranged in the o-, m- or especially the p-position with respect to the radical Y.

The functional groups, such as hydroxy, carboxy or amino groups, present in the compounds of the formula I are optionally protected by conventional protecting groups that are used in penem, penicillin, cephalosporin and peptide chemistry Such protecting groups protect the functional groups in question from undesired condensation reactions, substitution reactions and the like during the synthesis of the compound of the formula I from its precursors Such protecting groups can be removed readily, that is to say without undesirable side-reactions taking place, for example by solvolysis or reduction.

Protecting groups of this kind and the methods by which they are introduced and removed are described, for example, in J. F. W. McOmie, "Protective Groups in Organic Chemistry", Plenum Press, London, N.Y. 1973, T. W. Greene, "Protective Groups in Organic Synthesis", Wiley, N.Y. 1981, "The Peptides", vol. I, Schroeder and Luebke, Academic Press, London, N.Y. 1965, and in Houben-Weyl, "Methoden der Organischen Chemie", vol. 15/1, Georg Thieme Verlag, Stuttgart, 1974.

In compounds of the formula (I), a hydroxy group may be protected, for example, by an acyl radical. Suitable acyl radicals are, for example, lower alkoxycarbonyl that is unsubstituted or is substituted by halogen, for example 2-bromoethoxycarbonyl or 2,2,2-trichloroethoxycarbonyl, lower alkenyloxycarbonyl, for example allyloxycarbonyl, lower alkenyloxyoxalyl, for example allyloxyoxalyl, or phenyl-lower alkoxycarbonyl that is unsubstituted or is substituted by nitro, for example benzyloxycarbonyl or 4-nitrobenzyloxycarbonyl. Other suitable hydroxy-protecting groups are, for example, trisubstituted silyl, such as tri-lower alkylsilyl, for example trimethylsilyl, dimethyl-(2,3-dimethylbut-2-yl)-silyl or tert. -butyl-dimethylsilyl. Tri-lower alkylsilyl, lower alkenyloxyoxalyl and lower alkenyloxycarbonyl are preferred as hydroxy-protecting groups.

A carboxy group is customarily protected in esterified form, the ester group being readily cleavable under mild conditions, for example under mildly reductive, such as hydrogenolytic, or mildly solvolytic, such as acidolytic or especially basic or neutral hydrolytic, conditions.

Such esterified carboxy groups contain as esterifying groups especially lower alkyl groups that are branched in the 1-position or suitably substituted in the 1- or 2-position. Suitable carboxy groups in esterified form are, inter alia, benzyloxycarbonyl that is unsubstituted or is substituted by nitro or by lower alkoxy, such as methoxy, for example 4-nitrobenzyloxycarbonyl or 4-methoxybenzyloxycarbonyl, lower alkanoylmethoxycarbonyl, such as acetonyloxycarbonyl, halo-lower alkoxycarbonyl, such as 2-halo-lower alkoxycarbonyl, for example 2,2,2-trichloroethoxycarbonyl or 2-bromoethoxycarbonyl, lower alkenyloxycarbonyl, for example allyloxycarbonyl, or ethoxycarbonyl substituted in the 2-position by tri-lower alkylsilyl, for example 2-trimethylsilylethoxycarbonyl or 2-(di-n-butyl-methyl-silyl)-ethoxycarbonyl. Preferred protected carboxy groups are the 4-nitrobenzyloxycarbonyl and lower alkenyloxycarbonyl, especially allyloxycarbonyl, groups, and the ethoxycarbonyl group substituted in the 2-position by tri-lower alkylsilyl, for example by trimethylsilyl or di-n-butyl-methyl-silyl.

A protected amino group can be, for example, in the form of a readily cleavable acylamino group, nitro group or in the form of an azido group. In a corresponding acylamino group, acyl is, for example, the acyl radical of a lower alkanecarboxylic acid that is unsubstituted or is substituted, for example, by halogen or by phenyl, or especially of a carbonic acid semiester. Such acyl groups are, for example, lower alkenyloxycarbonyl, for example allyloxycarbonyl, unsubstituted or substituted benzyloxycarbonyl, for example 4-nitrobenzyloxycarbonyl, 2-halo-lower alkoxycarbonyl, for example 2,2,2-trichloroethoxycarbonyl, or 2-bromoethoxycarbonyl, or 2-(trisubstituted silyl)-ethoxycarbonyl, such as 2-trilower alkylsilylethoxycarbonyl, for example 2-trimethylsilylethoxycarbonyl or 2-(di-n-butyl-methyl-silyl)ethoxycarbonyl. Preferred protected amino groups are, for example, azido, nitro, lower alkenyloxycarbonylamino, for example allyloxycarbonylamino, and benzyloxycarbonylamino that is unsubstituted or is substituted by nitro.

Salts of compounds according to the invention are especially pharmaceutically acceptable, non-toxic salts of compounds of the formula I. Such salts are formed from the acidic carboxy groups $R_2$ present in compounds of the formula I, and are especially metal or ammonium salts, such as alkali metal and alkaline earth metal salts, for example sodium, potassium, magnesium or calcium salts, and ammonium salts with ammonia or suitable organic amines, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzylethylenediamine, dibenzylamine or N-benzyl-β-phenethylamine. Compounds of the formula I having a basic group, for example having an amino group $R_3$, can form acid addition salts, for example with inorganic acids, such as hydrochloric acid, sulphuric acid or phosphoric acid, or with suitable organic carboxylic or sulphonic acids, for example acetic acid, succinic acid, fumaric acid, maleic acid, tartaric acid, oxalic acid, citric acid, benzoic acid, mandelic acid, malic acid, ascorbic acid, methanesulphonic acid or 4-toluenesulphonic acid. Compounds of the formula I having an acidic and a basic group can also be in the form of internal salts, that is to say in zwitterionic form.

For the purposes of isolation or purification it is also possible to use pharmaceutically unsuitable salts. Only the pharmaceutically acceptable, non-toxic salts are used therapeutically and these are therefore preferred.

The penem compounds of the formula I may have an additional chiral centre in the radical $R_1$. For example, 1-hydroxyethyl as the radical $R_1$ may be in the R-, the S- or the racemic R,S-configuration. In preferred penem compounds of the formula I, a radical $R_1$ that has an asymmetric carbon atom, especially 1-hydroxyethyl, has the R-configuration. The invention relates accordingly to the pure diastereoisomers and mixtures of diastereoisomers of compounds of the formula I that have additional chiral centres in the radical $R_1$.

The compounds of the formula I have valuable pharmacological or can be used as intermediates for the manufacture of such compounds having valuable pharmacological properties. Compounds of the formula I in which functional groups are in unprotected form and pharmaceutically acceptable salts of such compounds having salt-forming groups have antibacterial activity. For example, they are effective in vitro against gram-positive and gram-negative cocci, including methicillin-resistant staphylococci, for example *Staphylococcus aureus, Staphylococcus epidermidis, Streptococcus pyogenes, Streptococcus pneumoniae* and *Streotococcus faecalis*, and *Haemophilus influenzae*, in minimum concentrations of less than 0.1 to approximately 8 μg/ml, and against Enterobacteriaceae, for example *Escherichia coli* and *Klebsiella pneumoniae, Pseudomonas aeruginosa* and anaerobes, such as *Bacteroides sp.*, in minimum concentrations of from 0.1 to approximately 64 μg/ml. *In vivo*, in the case of systemic infection of mice, for example by *Staphylococcus aureus* and *Escherichia coli*, upon subcutaneous or oral administration of compounds according to the invention, $ED_{50}$ values of from approximately 0.2 to approximately 30 mg/kg are obtained.

The novel compounds can be used as orally or parenterally administrable antibacterial antibiotics, for example in the form of corresponding pharmaceutical preparations, for the treatment of infections.

Compounds of the formula I in which at least one of the functional groups present is in protected form can be used as intermediates for the manufacture of the above-mentioned pharmacologically active compounds of the formula I.

The invention relates especially to the compounds of the formula I defined hereinbefore with the exception of those in which $R_1$ and $R_2$ have the meanings specified, $R_3$ is hydroxy, protected hydroxy, carbamoyloxy, halogen or heteroarylthio, each of $R_4$ and $R_5$, independently of the other, represents hydrogen, lower alkyl, halogen, carbamoyl, hydroxy, protected hydroxy, lower alkoxy, amino, protected amino or lower alkanoylamino, each of $A_1$ and $A_2$ represents methylene and Y represents a group of the formula —O— or —S—, the pure optical isomers of such compounds of formula I and mixtures of those optical isomers, and salts of such compounds of the formula I having a salt-forming group.

The invention relates more especially to compounds of the formula I in which $R_1$ is lower alkyl substituted in the α-position by hydroxy, $R_2$ is carboxy or esterified carboxy that is cleavable under physiological conditions, $R_3$ is hydrogen, amino or amino mono- or di-substituted by lower alkyl, hydroxy-lower alkyl, carbamoyl-lower alkyl, amino-lower alkyl, lower alkylamino-lower alkyl, di-lower alkylamino-lower alkyl, or by a heteroaryl, heteroaryl-lower alkyl and/or N-azaheterocyclyl-lower alkyl radical; or is sulphamoyl, aminomethyleneamino, guanidino, carbamoyl, hydroxy, lower alkoxy, halogen, carbamoyloxy, lower alkanoyl, N-azaheterocyclyl or heteroarylthio wherein heteroaryl is a monocyclic 5- or 6-membered heteroaryl radical that has from 1 to 4 ring nitrogen atoms and is bonded by way of a ring carbon atom, and N-azaheterocyclyl is a monocyclic 5-membered heteroaryl radical that has from 1 to 4 ring nitrogen atoms and is bonded by way of an uncharged ring nitrogen atom, a monocyclic partially saturated 6-membered heteroaryl radical that has from 1 to 3 ring nitrogen atoms and is bonded by way of an uncharged ring nitrogen atom, or a monocyclic saturated 5- or 6-membered azaheterocyclyl radical that has from 1 to 3 ring nitrogen atoms and optionally an additional ring hetero atom selected from the group comprising sulphur and oxygen, and that is bonded by way of an uncharged ring nitrogen atom, or is a benzo derivative thereof, which heteroaryl and N-azaheterocyclyl radicals are unsubstituted or are substituted by hydroxy, lower alkoxy, halogen, lower alkylthio, phenylthio, lower alkyl, hydroxy-lower alkyl, lower alkanoyloxy-lower alkyl, carboxy-lower alkyl, carbamoyl-lower alkyl, carbamoyloxy-lower alkyl, halo-lower alkyl, optionally N-lower alkylated amino-lower alkyl, for example amino-lower alkyl, lower alkylamino-lower alkyl or di-lower alkylamino-lower alkyl, lower alkanoylamino-lower alkyl, sulpho-lower alkyl, lower alkanoyl, unsubstituted or substituted amino, for example amino, lower alkylamino, di-lower alkylamino or lower alkanoylamino, by optionally functionally modified carboxy or sulpho, for example carboxy, lower alkoxy-carbonyl, carbamoyl, cyano, sulpho or sulphamoyl, pyridyl, such as 2-, 3- or 4-pyridyl, and-/or by phenyl or phenyl substituted by lower alkyl, lower alkoxy and/or by halogen, and N-azaheterocyclyl radicals having a disubstitutable ring carbon atom may also be substituted by oxo; each of $R_4$ and $R_5$, independently of the other, represents hydrogen, lower alkyl, hydroxy, lower alkoxy, halogen, amino, lower alkanoylamino or carbamoyl, or $R_4$ and $R_5$ together represent methylenedioxy, Y represents a group —O—, —S— or —$NR_6$—, $R_6$ is hydrogen or lower alkyl, $A_1$ is lower alkylene or unsubstituted phenylene or phenylene substituted by lower alkyl, hydroxy, lower alkoxy, amino or by halogen, and $A_2$ represents a direct bond or lower alkylene, the pure optical isomers of such compounds of the formula I and mixtures of those optical isomers, and salts of such compounds of the formula I having a salt-forming group.

The invention relates most especially to compounds of the formula I in which $R_1$ is hydroxymethyl or 1-hydroxyethyl, $R_2$ is carboxy or esterified carboxy that is cleavable under physiological conditions, $R_3$ is amino, methylamino, dimethylamino, (2-hydroxyethyl)amino, bis-(2-hydroxyethyl)-amino, (4-pyridyl)-amino, (3-pyridyl)-amino, morpholin-4-yl, piperazin-1-yl, 4-carbamoylpiperazin-1-yl, 3-hydroxy-4-oxo-1,4-dihydropyridin-1-yl, 1H-tetrazol-1-yl, pyridin-4-ylthio, 1-methyl-1H-tetrazol-5-ylthio, carbamoyl or carbamoyloxy, $R_4$ and $R_5$ represent hydrogen, Y represents a group —O—, $A_1$ is lower alkylene having 1 or 2 carbon atoms, and $A_2$ represents a direct bond or lower alkylene having 1 or 2 carbon atoms, the pure optical isomers of such compounds of the formula I and mixtures of those optical isomers, and salts of such compounds of the formula I having a salt-forming group.

The invention relates preferably to compounds of the formula I in which $R_1$ is 1-hydroxyethyl, $R_2$ is carboxy, $R_3$ represents amino, methylamino or dimethylamino, each of $R_4$ and $R_5$ represents hydrogen, Y represents a group —O—, $A_1$ is methylene, and $A_2$ is methylene or ethylene, the pure optical isomers of such compounds of the formula I and mixtures of those optical isomers, and salts thereof.

The invention relates especially to the compounds of the formula I mentioned in the Examples and their pharmaceutically acceptable salts.

The compounds of the present invention can be manufactured by processes that are known per se.

The novel compounds are manfactured, for example, as follows:

(a) in a compound of the formula

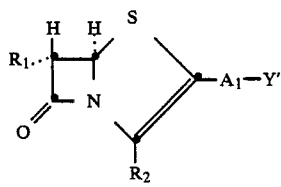

(II)

in which $R_1$, $R_2$ and $A_1$ have the meanings given under formula (I) and Y' represents a group that can be converted into the radical

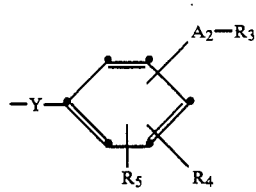

(IIa)

in which Y, $A_2$, $R_3$, $R_4$ and $R_5$ have the meanings given under formula (I), the group Y' is converted into the radical

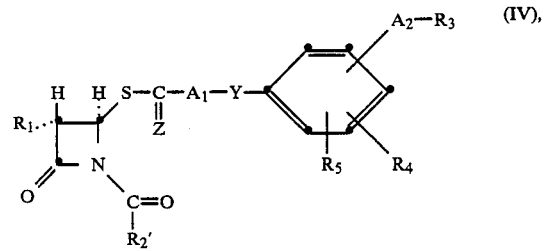

(IIa)

or (b) an ylide compound of the formula (III), in which $R_1$, $R_3$, $R_4$, $R_5$, $A_1$, $A_2$ and Y have the meanings given under formula I, $R_2'$ represents a protected carboxy group, Z represents oxygen or sulphur and $X\oplus$ represents either a trisubstituted phosphonio group or a diesterified phosphono group together with a cation, is cyclised, or (c) a compound of the formula (IV), in which $R_1$, $R_3$, $R_4$, $R_5$, $A_1$ A and Y have the meanings given under formula I, Z is oxygen or sulphur and $R_2'$ is a protected carboxy group, is treated with an organic compound of trivalent phosphorus, and, if desired or necessary, in a resulting compound of the formula I a protected functional group is converted into the free functional group, and/or, if desired, in a resulting compound of the formula I a free carboxy group $R_2$ is converted into an esterified carboxy group that is cleavable under physiological conditions, and/or, if desired, in a resulting compound of the formula I a radical $R_3$ is converted into a different radical $R_3$, and/or, if desired, a resulting mixture of isomeric compounds of the formula I is separated into the individual isomers, and/or, if desired, a resulting compound having a salt-forming group is converted into a salt or a resulting salt is converted into the free compound or into a different salt.

In the starting compounds of the formulae II–IV, functional groups, such as free hydroxy groups, for example in the radical R₁, and free amino groups are preferably protected by conventional protecting groups, for example by those mentioned above.

(a) REACTION OF THE COMPOUND OF THE FORMULA II

A group Y' that can be converted into the radical

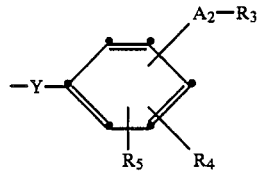
(IIa)

is, for example, hydroxy or a group that can be exchanged by nucleophilic reaction.

Thus, compounds of the formula I in which Y is a group —O— can be manufactured by reacting a compound of formula II in which Y' represents hydroxy with a phenol of the formula

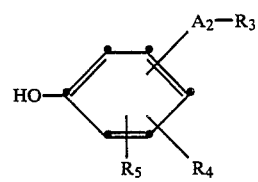
(Va)

in the presence of an organic compound of trivalent phosphorus, such as a tri-lower alkylphosphine, for example tri-n-butylphosphine, a tri-lower alkylphosphite, for example triethylphosphite, or triphenylphosphine, and in the presence of an azodicarboxylic acid diester, such as a corresponding tri-lower alkyl ester, for example azodicarboxylic acid diethyl ester, in an inert aprotic solvent, such as a cyclic ether, for example tetrahydrofuran or dioxan, at room temperature or at reduced or slightly elevated temperature, for example in a temperature range of from approximately −70° to approximately 40° C., preferably at from approximately 0° to approximately 20° C.

Compounds of the formula I in which Y represents a group of the formula —S— or —NR₆— can be manufactured from compounds of formula II in which Y' represents a group that can be exchanged by nucleophilic reaction. Such groups Y' that can be exchanged by nucleophilic reaction are especially esterified hydroxy groups, such as hydroxy groups esterified by a hydrohalic acid, a lower alkylsulphuric acid, a di-lower alkylphosphoric acid or diarylphosphoric acid, a lower alkanecarboxylic acid that is unsubstituted or is substituted by oxo or by halogen, a lower alkanesulphonic acid that is unsubstituted or is substituted by halogen, or by a benzenesulphonic acid that is unsubstituted or is substituted by halogen or lower alkyl Such groups Y' are, for example, halogen, such as chlorine, bromine or iodine, lower alkyl sulphate, for example methyl sulphate or ethyl sulphate, di-lower alkylphosphoryloxy or diarylphosphoryloxy, for example dimethylphosphoryloxy, diethylphosphoryloxy or diphenylphosphoryloxy, lower alkanoyloxy that is unsubstituted or is substituted by halogen or by oxo, for example formyloxy, acetoxy or acetoacetoxy, lower alkanesulphonyloxy that is unsubstituted or is substituted by halogen, for example methanesulphonyloxy or trifluoromethanesulphonyloxy, or benzenesulphonyloxy optionally substituted by halogen or by lower alkyl, for example benzenesulphonyloxy, 4-chlorobenzenesulphonyloxy, 4-bromobenzenesulphonyloxy or 4-methylbenzene-sulphonyloxy.

The reaction of a compound of the formula (II) in which Y' is a group that can be exchanged by nucleophilic reaction is carried out, for example, with a compound of the formula

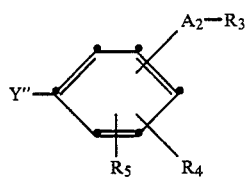
(Vb)

in which an amino group which may be present in the radical R₃ is in protected form and Y'' represents a group HS— or HN(R₆)—, in the presence of at least equimolar amounts of a basic condensation agent, for example an alkali metal lower alkoxide, for example sodium methoxide or potassium tert.-butoxide, or of an alkali metal hydride or amide, for example sodium hydride or sodium amide, in an inert solvent, for example an ether, such as dioxan or tetrahydrofuran, or an amide, for example formamide or dimethylformamide, and, when using alkali metal lower alkoxides, also in the corresponding lower alkanol, or in a mixture of inert solvents, at room temperature or reduced or slightly elevated temperature, for example at from approximately −60° C. to approximately +40° C., especially at from approximately −20° to approximately +30° C., if necessary in an inert gas atmosphere, such as a nitrogen atmosphere.

(b) CYCLISATION OF THE COMPOUND OF THE FORMULA III

The group X⊕ in the starting material of the formula III is one of the phosphonio or phosphono groups customarily used in Wittig condensation reactions, especially a triarylphosphonio group, for example a triphenylphosphonio group, or a tri-lower alkyl-phosphonio group, for example a tri-n-butylphosphonio group, or a phosphono group diesterified by lower alkyl, for example ethyl, the symbol X⊕ in the case of the phosphono group including, in addition, the cation of a strong base, especially a suitable metal ion, such as an alkali metal ion, for example the lithium, sodium or potassium ion. Preferred as the group X⊕ are, on the one hand, triphenylphosphonio and, on the other hand, diethylphosphono together with an alkali metal ion, for example the sodium ion.

Cyclisation may take place spontaneously, that is to say during the manufacture of the starting materials, or may be effected by heating, for example in a temperature range of approximately from 30° C. to 160° C., preferably from approximately 80° C. to approximately 130° C. The reaction is preferably carried out in a suitable inert solvent, such as an aliphatic, cyclo-aliphatic or aromatic hydrocarbon, for example cyclohexane, benzene or toluene, and, if necessary, in an inert gas atmosphere, for example a nitrogen atmosphere.

(c) CYCLISATION OF THE COMPOUND OF THE FORMULA IV

An organic compound of trivalent phosphorus is derived, for example, from phosphorous acid and is especially an ester thereof with a lower alkanol, for example methanol or ethanol, and/or with an unsubstituted or substituted aromatic hydroxy compound, for example phenol or pyrocatechol, or is an amide ester thereof of the formula $P(OR_a)_2N(R_b)_2$ in which each of $R_a$ and $R_b$, independently of the other, represents lower alkyl, for example methyl, or aryl, for example phenyl. Preferred compounds of trivalent phosphorus are tri-lower alkyl phosphites, for example trimethyl phosphite or triethyl phosphite.

The reaction is preferably carried out in an inert solvent, such as an aromatic hydrocarbon, for example benzene or toluene, an ether, for example dioxan or tetrahydrofuran, or a halogenated hydrocarbon, for example methylene chloride or chloroform, at a temperature of approximately from 20° to 140° C., preferably from approximately 40° to approximately 110° C., one molar equivalent of a compound of the formula IV being reacted with two molar equivalents of the phosphorus compound. Preferably, the compound of the formula IV is placed in an inert solvent and the phosphorus compound, preferably dissolved in the same inert solvent, is added dropwise over a prolonged period, for example over a period of from 2 to 4 hours.

In a preferred form of the process, the starting material of the formula IV is manufactured as indicated further below and, without being isolated from the reaction mixture, is reacted with the organic compound of trivalent phosphorus, producing the end products of the formula I.

The starting materials of the formulae II–V used are preferably those which result in the compounds of formula I mentioned at the beginning as being especially preferred.

In a resulting compound of the formula I in which one or more functional groups are protected, these groups, for example protected carboxy, hydroxy and/or amino groups, can be freed, optionally in stages or simultaneously, in a manner known per se by means of solvolysis, especially hydrolysis, alcoholysis or acidolysis, or by means of reduction, especially hydrogenolysis or chemical reduction.

In a compound of the formula I obtainable according to the process in which $R_2$ represents a protected carboxy group, the protected carboxy group can be freed in a manner known per se. For example, ethoxycarbonyl substituted in the 2-position by a trisubstituted silyl group can be converted into free carboxy, for example, by treatment with a carboxylic acid, such as formic acid or trifluoroacetic acid, optionally with the addition of a nucelophilic compound, such as phenol or anisole Unsubstituted or substituted benzyloxycarbonyl can be cleaved, for example, by means of hydrogenolysis, that is to say by treatment with hydrogen in the presence of a metallic hydrogenation catalyst, such as a palladium catalyst. Furthermore, suitably substituted benzyloxycarbonyl, such as 4-nitrobenzyloxycarbonyl, can be converted into free carboxy also by chemical reduction, for example by treatment with an alkali metal dithionite, for example sodium dithionite, or with a reducing metal, for example tin, customarily in the presence of a hydrogen-yielding agent that together with the metal is capable of producing nascent hydrogen, such as a suitable carboxylic acid, for example a lower alkanecarboxylic acid that is unsubstituted or is substituted, for example, by hydroxy, for example acetic acid, or an alcohol or thiol, it being preferable to add water. The removal of an allyl protecting group can be effected, for example, by reaction with a palladium compound, for example tetrakis-(triphenylphoshine)-palladium, optionally in the presence of triphenylphosphine and with the addition of an allyl group acceptor, such as a carboxylic acid, for example 2-ethylhexanoic acid, or a salt thereof, or dimedone or tributyltin hydride. By treatment with a reducing metal or metal salt, as described above, it is also possible to convert 2-halolower alkoxycarbonyl (optionally after converting a 2-bromo-lower alkoxycarbonyl group into a corresponding 2-iodo-lower alkoxycarbonyl group) into free carboxy. Substituted 2-silylethoxycarbonyl can be converted into free carboxy also by treatment with a salt of hydrofluoric acid that yields the fluoride anion, such as an alkali metal fluoride, for example sodium fluoride, in the presence of a macrocyclic polyether ("Crown ether") or with a fluoride of an organic quaternary base, such as tetra-lower alkylammonium fluoride, for example tetrabutylammonium fluoride.

On the other hand, also compounds of the formula I in which $R_2$ represents carboxy can be converted into compounds of the formula I in which $R_2$ represents an esterified carboxy group that is cleavable under physiological conditions Thus, the free carboxy group can be esterified, for example, by reaction with a corresponding alcohol in the presence of an esterifying agent, such as a carbodiimide, for example dicyclohexylcarbodiimide, or carbonyldiimidazole. Such esters can be manufactured also by reaction of a salt of the acid, which salt is optionally manufactured in situ, with a reactive ester of a corresponding alcohol and a strong inorganic acid, such as sulphuric acid, or a strong organic sulphonic acid, such as 4-toluenesulphonic acid In compounds of the formula I obtainable according to the process in which the radical $R_1$ contains protected hydroxy as substituent, the protected hydroxy group can be converted into the free hydroxy group in a manner known per se. For example, a hydroxy group protected by a suitable acyl group or by an organic silyl group is freed in the same manner as a correspondingly protected amino group (see below); a tri-lower alkylsilyl group can be removed, for example, also with tetrabutylammonium fluoride and acetic acid (under these conditions, carboxy groups protected by trisubstituted silylethoxy are not cleaved).

In a compound of the formula I obtainable according to the invention having a protected amino group, this group can be converted into the free amino group in a manner known per se, for example, depending on the nature of the protecting group, preferably by means of solvolysis or reduction. For example, 2-halo-lower alkoxycarbonylamino (optionally after converting a 2-bromo-lower alkoxycarbonylamino group into a 2-iodo-lower alkoxycarbonylamino group) or 4-nitrobenzyloxycarbonylamino can be cleaved by treatment with a suitable chemical reducing agent, such as zinc in the presence of a suitable carboxylic acid, such as aqueous acetic acid, or by catalysis with hydrogen in the presence of a palladium catalyst. 4-nitrobenzyloxycarbonylamino can be cleaved also by treatment with an alkali metal dithionite, for example sodium dithionite. Allyloxycarbonylamino can be cleaved by reaction with a palladium compound, for example tetrakis-(triphenylphosphine)-palladium, optionally in the presence of triphenylphosphine and in the presence of an allyl group acceptor, such as a carboxylic acid, for example 2-ethylhexanoic acid, or a salt thereof, or dimedone or tributyltin hydride. An amino group protected by 2-substituted silylethoxycarbonyl can be converted into a free amino group by treatment with a salt of hydrofluoric acid that yields the fluoride anion, such as an alkali metal fluoride, for example sodium fluoride, in the presence of a macrocyclic polyether ("Crown ether") or with a fluoride of an organic quaternary base, such as tetra-lower alkylammonium fluoride, for example tetraethylammonium fluoride. An amino group protected in the form of a nitro or azido group is converted into free amino, for example, by reduction, for example by catalytic hydrogenation with hydrogen in the presence of a hydrogenation catalyst, such as platinum oxide or palladium, or by treatment with zinc in the presence of an acid, such as acetic acid.

Furthermore, in compounds of the formula I that are obtainable according to the process, a radical $R_3$ can be converted into a different radical $R_3$.

For example, in a compound of formula I in which $A_2$ is lower alkylene and $R_3$ represents halogen, halogen can be exchanged for unsubstituted or substituted amino or heteroarylthio by reacting the halogen compound I in an inert solvent at room temperature or reduced temperature, for example in a temperature range of from approximately $-20°$ to approximately $30°$ C., with ammonia, a corresponding amine or a heteroarylmercaptan, in which reaction, in order to bind the hydrohalic acid being liberated, at least equimolar amounts of an inorganic base, such as an alkali metal hydroxide, hydrogen carbonate or carbonate, or an organic base, such as a tertiary amine, for example triethylamine, N,N-dimethylaniline or pyridine, are added.

In compounds of the formula I in which $R_3$ is hydroxy, the hydroxy group can be converted into a carbamoyloxy group. For this conversion the hydroxy compound I, in which additional functional groups, such as especially a hydroxy group in the radical $R_1$, are in protected form, is reacted at room temperature in an inert solvent, for example a lower alkyl ether or methylene chloride, with carbamoyl chloride or trichloroacetyl isocyanate. The N-trichloroacetylcarbamoyloxy compound which is produced first if trichloroacetyl isocyanate is used is converted into the desired carbamoyloxy compound by solvolysis using a lower alkanol, for example methanol, optionally in the presence of silica gel at room temperature.

Compounds of the formula I in which $R_3$ is amino can be converted into other compounds of the formula I in which $R_3$ is aminomethyleneamino or guanidino. The conversion can be carried out, for example, according to one of methods mentioned in German Offenlegungsschrift No. 2652679. For example, compounds of the formula I in which $R_3$ is amino can be converted by reaction with ethyl formimidate, or with an isothiourea of the formula $(NH_2, Y_1)C=NH$ in which $Y_1$ is lower alkylthio, for example ethylthio, into compounds of the formula I in which $R_3$ is aminomethyleneamino or guanidino, respectively. In compounds of the formula I in which $R_3$ is amino, the amino group can also be converted into a dimethylamino group, for example by reaction with formalin and a lithium hydride or a borohydride, such as sodium cyanoborohydride.

Salts of compounds of the formula I having salt-forming groups can be manufactured in a manner known per se. For example, salts of compounds of the formula I having a free carboxy group can be formed, for example, by treatment with metal compounds, such as inorganic alkali metal salts or alkaline earth metal salts, for example sodium hydrogen carbonate, or with ammonia or with a suitable organic amine, it being preferable to use stoichiometric amounts or only a small excess of the salt-forming agent. Acid addition salts of compounds of the formula I are obtained in customary manner, for example by treatment with a suitable acid or a suitable anion-exchange reagent Internal salts of compounds of the formula I can be formed, for example, by neutralising salts, such as acid addition salts, to the isoelectric point, for example with weak bases, or by treatment with ion-exchangers.

Salts can be converted into the free compounds in customary manner: metal and ammonium salts, for example by treatment with suitable acids, and acid addition salts, for example by treatment with a suitable basic agent.

Resulting mixtures of isomeric compounds can be separated into the individual isomers according to methods that are known per se. For example, a resulting racemate can be reacted with an optically active auxiliary, the resulting mixture of two diastereoisomeric compounds can be separated with the aid of suitable physico-chemical methods (for example fractional crystallisation, adsorption chromatography) and the individual diastereoisomeric compounds can then be split into the optically active compounds.

In all subsequent conversions of resulting compounds of the formula I, those reactions are preferred which take place under moderately alkaline conditions or, especially, neutral conditions.

The process also includes those embodiments according to which compounds formed as intermediates are used as starting materials and the remaining process steps are carried out with them, or the process is discontinued at any stage. Furthermore, starting materials can be used in the form of derivatives or can be formed in situ, optionally under the reaction conditions.

The starting compounds of the formulae III and IV can be manufactured as indicated in the following Reaction Scheme I:

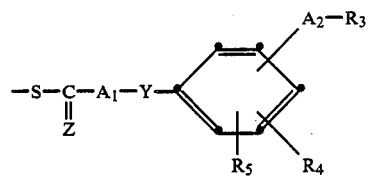

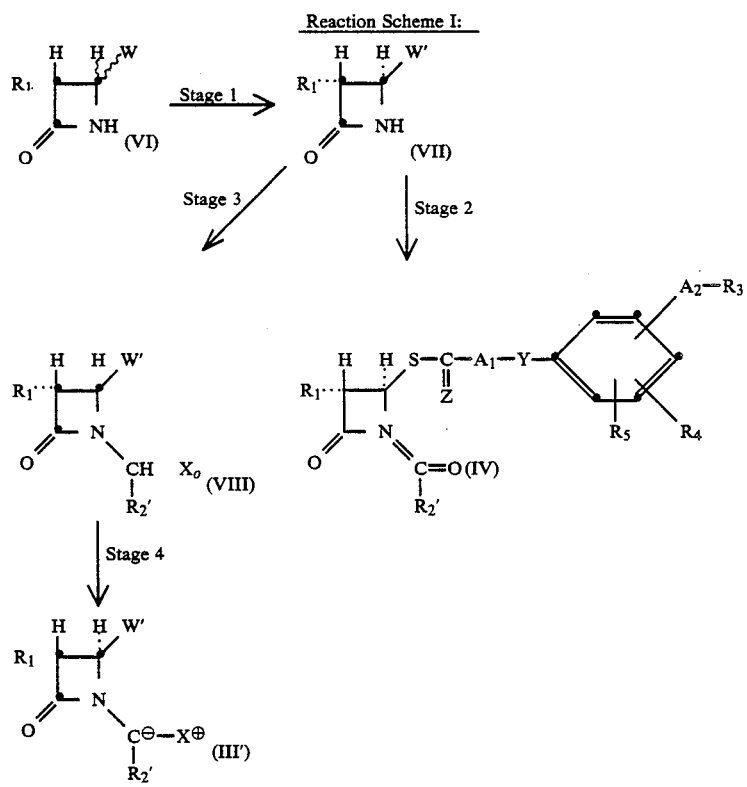

In compounds of the formulae III', VII and VIII, W' represents the radical

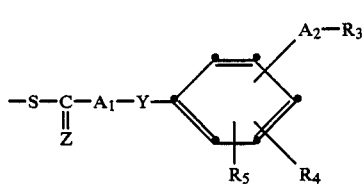

or triphenylmethylthio or lower alkanoylthio.

STAGE 1

Suitable starting compounds of the formula VI in which W represents a radical that is readily exchangeable by nucleophilic reaction, for example lower alkanoyloxy, such as acetoxy, or sulphonyloxy $R_o$—$SO_2$—, in which $R_o$ is, for example, lower alkyl that is unsubstituted or is substituted by hydroxy, such as methyl, tert.-butyl or 2-hydroxyethyl, are known, for example, from published European Patent Application No. 82113, German Offenlegungsschrift No. 3 224 055 and German Offenlegungsschrift No. 3 013 997, or can be manufactured in a manner analogous thereto.

A compound that introduces the radical is, for example, an acid of the formula

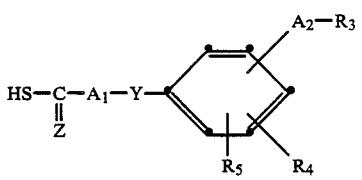

or especially a salt thereof, for example an alkali metal salt, such as the sodium or potassium salt, thereof. The substitution may be carried out in an organic solvent, such as in a lower alkanol, a lower alkanecarboxylic acid amide, a cyclic ether, or in a similar inert solvent at room temperature or at slightly elevated or reduced temperature, for example at from approximately 0° to approximately 40° C. The introduction of a triphenylmethylthio or lower alkanoylthio radical W' is effected in an analogous manner by reaction with an alkali metal salt, for example the sodium salt, of a thio-lower alkanecarboxylic acid, for example thioacetic acid, or of triphenylmethylmercaptan.

STAGE 2

A starting compound of the formula (IV) is obtained by treating an azetidinone of the formula (VII) in which W' represents the radical

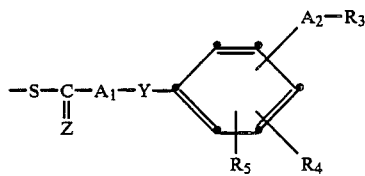

with an acid of the formula $R_2'$-COOH or especially a reactive derivative, such as an ester or acid halide, for example the acid chloride, thereof at a temperature of from $-50°$ to $80°$ C., preferably at from $-20°$ to $0°$ C., in an inert solvent, such as one of those mentioned for the reaction of compounds of the formula (IV) to form compounds of the formula I. When using an acid halide, the operation is preferably carried out in the presence of an acid-binding agent, such as a tertiary aliphatic amine, an aromatic amine, or especially a carbonate or hydrogen carbonate of an alkali metal or alkaline earth metal.

Compounds of the formula (VII) in which W' represents triphenylmethylthio or lower alkanoylthio can be converted into the starting compounds of the formula VII in which W' represents the radical

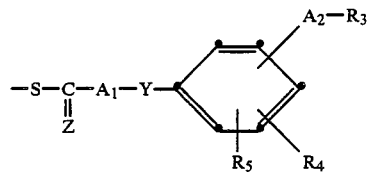

by reacting them in the presence of a base, for example pyridine or tri-n-butylamine, in a suitable solvent, for example diethyl ether or methanol, with a salt of the formula MA in which M represents a transition metal cation, especially the silver cation, and A represents a customary anion that favours the solubility of the salt MA in the chosen solvent, for example the nitrate, acetate or fluoride anion, and by treating the resulting salt of the formula

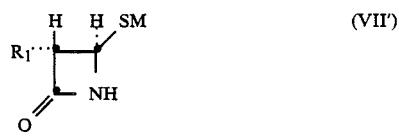

with an acylating agent that introduces the radical

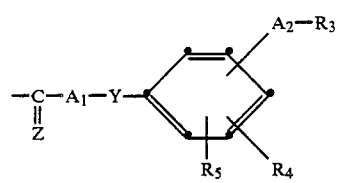

for example with the acid

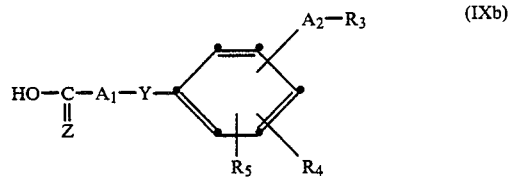

or with a reactive functional derivative, such as an acid halide, for example the chloride or bromide, azide or anhydride, thereof. If a reactive functional derivative of the acid of the formula (IXb), for example the acid chloride, is used, the acylation is effected in an inert solvent, such as a chlorinated hydrocarbon, or an ether, at room temperature or while heating or cooling, for example in a temperature range of from approximately $-50°$ to approximately $+60°$ C., especially at from approximately $-30°$ to approximately $+20°$ C.

STAGE 3

Compounds of the formula VIII in which $X_o$ represents a reactive esterified hydroxy group, especially halogen, for example chlorine or bromine, are manufactured by reacting a compound of the formula VII with a glyoxylic acid compound of the formula $R_2'$—CHO or a suitable derivative thereof, such as a hydrate, hemihydrate or hemiacetal, for example a hemiacetal of a lower alkanol, for example methanol or ethanol, and, in a resulting compound of the formula VIII in which $X_o$ represents hydroxy, converting the hydroxy group into a reactive esterified hydroxy group. The compounds of the formula VIII are usually obtained in the form of a mixture of the two isomers [with respect to the grouping -CH($R'_2$)~$X_o$].

The addition of the glyoxylic acid ester compound to the nitrogen atom of the lactam ring in the compound of the formula VII takes place at room temperature or, if necessary, while heating. When using the hydrate of the glyoxylic acid compound, water is formed which, if necessary, is removed by distillation, for example azeotropic distillation, or by using a suitable dehydrating agent. The operation is preferably carried out in the presence of a suitable inert solvent or solvent mixture.

The conversion of a hydroxy group $X_o$ into a reactive esterified hydroxy group $X_o$ in a compound of the formula VIII is carried out by treatment with a suitable esterifying agent, for example with a thionyl halide, for example thionyl chloride, preferably in the presence of a basic, especially organic basic, agent, such as an aliphatic tertiary amine, or a heterocyclic base of the pyridine type The operation is preferably carried out in the presence of a suitable solvent, for example dioxan or tetrahydrofuran, or a solvent mixture, if necessary while cooling, for example at from approximately $-30°$ to approximately $30°$ C.

STAGE 4

The starting material of the formula III is obtained by treating a compound of the formula VIII with a suitable phosphine compound, such as a tri-lower alkylphosphine, for example tri-n-butylphosphine, or a triarylphosphine, for example triphenylphosphine, or with a suitable phosphite compound, such as a tri-lower alkyl phosphite, for example triethyl phosphite, or an alkali metal di-lower alkyl phosphite, for example an alkali metal diethyl phosphite, and by converting a resulting compound of the formula III' in which W' represents triphenylmethylthio or lower alkanoylthio into a compound of the formula III' (=III) in which W' represents the radical

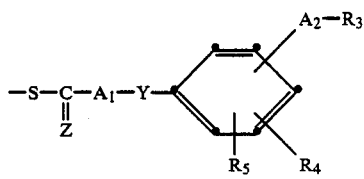

The reaction with the phosphine or phosphite compound is preferably carried out in a suitable inert solvent, such as a hydrocarbon, or an ether, or in a solvent mixture Depending on the reactivity, the reaction is carried out while cooling or at elevated temperature, approximately between $-10°$ and $+100°$ C., preferably at approximately from $20°$ to $80°$ C. The reaction is customarily carried out in the presence of a basic agent, such as an organic base, for example an amine, or "polystyrene Hunig base", or an inorganic base, for example an alkali metal carbonate, the initially formed phosphonium compound of the formula

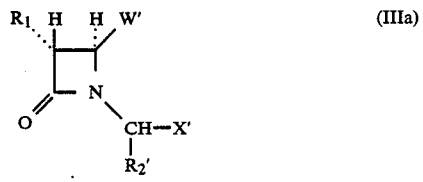

in which X' represents a phosphono group or a phosphonio group together with an anion, depending on the meaning of the radical $X_o$ (see formula VIII), for example, chloride, being converted into the ylide starting material of the formula III.

The introduction of the radical

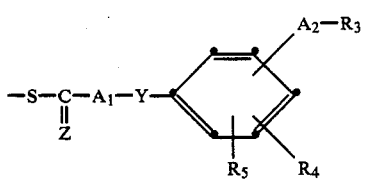

into compounds of the formula III' in which W' represents lower alkanoylthio or triphenylmethylthio can be effected in a manner analogous to that described in Stage 2.

The starting compounds of the formula II are known or can be manufactured, for example, by cyclising a phosphorane of the formula

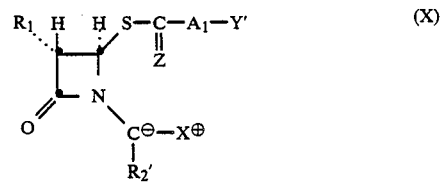

which can be synthesised in a manner analogous to that indicated in Reaction Scheme I, for example as described under process (b).

The starting compounds required for forming the side chain in the 2-position of the penem compounds according to the invention, for example those of the formulae V$a$, V$b$, IX$a$ and IX$b$, are known or can be manufactured analogously to the methods described in the literature.

The process described in Reaction Scheme I for the manufacture of compounds of the formulae (III), (IV), (VII) and (VIII), and also the process indicated for the manufacture of the compounds of the formula (II) and of the end products of the formula (I), can also be carried out using optically inactive compounds, and, at any stage of the process, the optically active compounds according to the present invention can be isolated in known manner from a resulting diastereoisomeric mixture or racemate.

The invention relates also to the novel starting materials and to novel intermediates obtainable according to the process, such as those of the formulae III, IV, and VII and VIII (wherein W' represents the radical

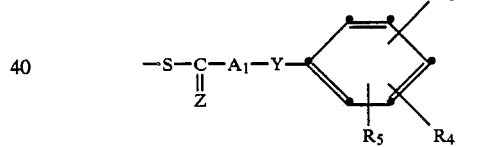

and to the processes indicated for the manufacture thereof.

The starting materials used and the reaction conditions chosen are preferably those which result in the compounds of the formula I described hereinbefore as being especially preferred.

The pharmacologically acceptable compounds of the present invention can be used, for example, for the manufacture of pharmaceutical preparations that contain a therapeutically effective amount of the active ingredient together or in admixture with inorganic or organic, solid or liquid pharmaceutically acceptable carriers that are suitable for oral or for parenteral, that is to say, for example, intramuscular, intravenous, subcutaneous or intraperitoneal, administration.

For oral administration there are used tablets or gelatine capsules that contain the active ingredient together with diluents, for example lactose, dextrose, sucrose, mannitol, sorbitol, cellulose and/or glycine, and lubricants, for example silica, talc, stearic acid or salts thereof, such as magnesium or calcium stearate, and/or polyethylene glycol. Tablets also contain binders, for example magnesium aluminium silicate, starches, such as maize, wheat, rice or arrowroot starch, gelatine, tragacanth, methylcellulose, sodium carboxymethylcellulose and/or polyvinylpyrrolidone, and, if desired, disintegrators, for example starches, agar, alginic acid or salts thereof, such as sodium alginate, and/or effervescent mixtures or adsorbents, colouring substances, flavourings or sweeteners.

For parenteral administration there are suitable especially infusion solutions, preferably isotonic aqueous solutions or suspensions, it being possible to prepare these before use, for example from lyophilised preparations that contain the active ingredient on its own or together with a carrier, for example mannitol. Such preparations may be sterilised and/or may contain adjuncts, for example preservatives, stabilisers, wetting agents and/or emulsifiers, solubilisers, salts for regulating the osmotic pressure and/or buffers.

The pharmaceutical preparations in question, which if desired, may contain other pharmacologically valuable substances, are manufactured in a manner known per se, for example by means of conventional mixing, dissolving or lyophilising processes, and contain approximately from 0.1% to 100%, especially from approximately 1% to approximately 50% or, in the case of lyophilisates, up to 100%, active ingredient Depending upon the type of infection and the condition of the infected organism, the dose (oral or parenteral) used for the treatment of warm-blooded animals (humans and animals) weighing approximately 70 kg is from approximately 100 mg to approximately 1000 mg b.i.d. or t.i.d..

The following Examples serve to illustrate the invention. Temperatures are given in degrees Celsius.

EXPERIMENTAL SECTION

Example 1:

(5R,6S)-2-[4-(N-allyloxycarbonylamino-methyl)-phenoxymethyl]-6-[(1R)
-1-allyloxy-carbonyloxyethyl]-2-penem-3carboxylic acid allyl ester.

A solution of 8.4 g of 2-[(3S,4R)-3-[(1R)-1-allyloxycarbonyloxyethyl]-4-[4-(N-allyloxycarbonylamino-methyl)-phenoxyacetylthio]-2-oxo-azetidin-1-yl]-2-triphenylphosphoranylideneacetic acid allyl ester in 750 ml of toluene is stirred at reflux temperature for 45 minutes under an argon atmosphere. The solvent is then evaporated off and the crude product is purified by chromatography on silica gel.

$R_f$ (eluant toluene/ethyl acetate 1:1)=0.6;
IR (CH$_2$Cl$_2$): 3440, 1793, 1745, 1720, 1590 cm$^{-1}$.

The starting material can be manufactured as follows:

a. 4-(N-allyloxycarbonylaminomethyl)-phenoxyacetic acid 0.97 g of 4-aminomethylphenoxyacetic acid is suspended in 15 ml of water, 2.4 ml of 5N NaOH solution are added thereto and, after cooling with ice, 0.63 ml of chloroformic acid allyl ester is added thereto over a period of 5 minutes After removing the cooling bath, the reaction mixture is stirred at room temperature for 20 minutes. The reaction mixture is then washed twice with ethyl acetate, and the aqueous phase is adjusted to pH 2 with 4N HCl and extracted with ethyl acetate. The organic solution is washed with brine and dried over sodium sulphate. The title compound is obtained after evaporating off the solvent.

TLC (ethyl acetate/acetic acid 95:5) $R_f$=0.4.

b. 2-[(3S,4R)-3-[(1R)-1-allyloxycarbonyloxyethyl]-4[4-4-(N-allyloxycarbonylaminomethyl)-phenoxyacetylthio)-2-oxo-azetidin-1-yl]-2-triphenylphosphoranylidene-acetic acid allyl ester 18.5 g of the silver salt of 2-[(3S,4R)-3-[(1R)-1-allyloxycarbonyloxyethyl]-4-mercapto-2oxo-azetidin-1-yl]-2-triphenylphosphoranylideneacetic acid allyl ester are dissolved in 320 ml of methylene chloride and, at 0°, 4.36 ml of pyridine, 100 mg of 4-dimethylaminopyridine and then, dropwise, a solution of 12 g of 4-(N-allyloxycarbonylaminomethyl)-phenoxyacetyl chloride in 210 ml of methylene chloride are added thereto After stirring for 20 minutes at 0°, the solid material is filtered off over Hyflo, and the filtrate is washed with aqueous sodium hydrogen carbonate solution and then with saturated NaCl solution. After drying over Na$_2$SO$_4$, the solvent is evaporated off. The residue is purified by chromatography on silica gel (eluant toluene to toluene-/ethyl acetate 75:25) R$_{=0.33}$. IR (CH$_2$Cl$_2$): 3440, 1760, 1720, 1695 cm$^{-1}$.

Example 2:

(5R,6S)-2-[4-(aminomethyl)-phenoxymethyl]-6-[(1R)-1-hydroxyethyl]-2-penem-3-carboxylic acid.

43 mg of tetrakis-triphenylphosphine-palladium and 1.51 ml of tributyltin hydride are added in portions to a solution of 0.528 g of (5R,6S)-2-[4-(N-allyloxy-carbonylaminomethyl)-phenoxymethyl]-6[(1R)-1-allyloxycarbonyloxyethyl]-2-penem-3-carboxylic acid allyl ester in 14 ml of absolute THF After stirring for 1.5 hours at room temperature, 0.32 ml of acetic acid is added dropwise to the mixture and the whole is stirred for a further 15 minutes. 15 ml of hexane are added to the reaction mixture. After centrifuging and decanting off the liquid, the residue, after being washed again with hexane, is triturated with water and filtered off. The filtration residue is washed 5 times more with approximately 10 ml of water. The collected filtrate is concentrated in a rotary evaporator and the title compound is obtained by chromatography on OPTI UPC$_{12}$ (eluant: water).

TLC (OPTI UPC$_{12}$; water) $R_f$=0.5;
IR (DMSO-d$_6$): 3445, 2970, 1774, 1613, 1583 cm$^{-1}$;
UV (water): $\lambda_{max}$=307 nm.

Example 3:

(5R,6S)-2-(4-fluorophenoxymethyl)-6-[(1R)-1-allyloxycarbonyloxyethyl]-2-penem-3-carboxylic acid allyl ester Analogously to Example 1, 1.2 g of 2-[(3S,4R)-3[(1R)-1allyloxycarbonyloxyethyl]-4-(4-fluoro-phenoxy-acetylthio)-2-oxo-azetidin-1-yl]-2-triphenyl-phosphoran-ylideneacetic acid allyl ester in 750 ml of toulene are reacted to form the title compound.

IR ($CH_2Cl_2$): 1795, 1747, 1705, 1650, 1580 $cm^{-1}$.

The starting material is manufactured as follows:

1.74 g of the silver salt of 2-[(3S,4R)-3-[(1R)-1allyloxycarbonyloxyethyl]-4-mercapto-2-oxo-azetidin-1-yl]-2-triphenylphosphoranylideneacetic acid allyl ester are reacted in 30 ml of methylene chloride with 0.41 ml of pyridine, 20 mg of 4-dimethylaminopyridine and 0.7 g of 4-fluorophenoxyacetyl chloride. After working up analogously to Example 1, 2-[(3S,4R)-3-[(1R)-1-allyloxycarbonyloxyethyl]-4-(4-fluorophenoxyacetylthio)-2-oxo-azetidin-1-yl]-2-triphenylphosphoranylideneacetic acid allyl ester is obtained.

IR ($CH_2Cl_2$): 1755, 1690 $cm^{-1}$.

Example 4:

The sodium salt of (5R,6S)-2-(4-fluorophenoxymethyl)-6-[(1R)-1-hydroxyethyl]-2penem-3-carboxylic acid 204 mg of 1,3-dimethylbarbituric acid and 36 mg of tetrakis-triphenylphosphine-palladium are added at room temperature to 604 mg of (5R,6S)-2-(4-fluorophenoxymethyl-6-[(1R)-1-allyloxycarbonyloxyethyl]2-penem-3-carboxylic acid allyl ester in 11 ml of tetrahydrofuran. After stirring for 25 minutes at room temperature, the reaction mixture is concentrated under a high vacuum and then taken up in ethyl acetate/water, the aqueous phase having been adjusted beforehand to pH 7.0 with sodium hydrogen carbonate. After separating off the organic phase and again washing with ethyl acetate, the aqueous layer is concentrated in a rotary evaporator, and the pure title substance is isolated by subsequent column chromatography on OPTI-UPC$_{12}$ (solvent: water). TLC (OPTI, UPC$_{12}$; water/acetonitrile 4:1) $R_f$=0.39; IR (DMSO-d$_6$): 1771, 1618, 1587 $cm^{-1}$; UV (water): $\lambda_{max}$=307 nm.

Example 5:

(5R,6S)-pivaloyloxymethyl-2-(4-fluorophenoxymethyl)-6-[(1R)-1-hydroxyethyl]-2-penem-3-carboxylate 90 mg of the sodium salt of (5R,6S)-2-(4-fluorophenoxymethyl)-6-[(1R)-1-hydroxyethyl]-2-penem-3-carboxylic acid are dissolved in 2 ml of absolute DMF; the solution is cooled to 0° and 67 μl of iodomethyl pivalate are added. After stirring for 45 minutes at 0°, the reaction mixture is diluted with ethyl acetate, washed three times with saturated aqueous sodium chloride solution and dried over $Na_2SO_4$. After filtration and concentration, the crude product is purified by chromatography on silica gel (solvent: toluene to toluene/ethyl acetate 85:15).

IR ($CH_2Cl_2$): 1795, 1750, 1730, 1585 $cm^{-1}$;

UV (ethanol): $\lambda_{max}$=328 nm.

Example 6:

(5R,6S)-2-(4-allyloxycarbonylaminophenoxymethyl]-6-[(1R)-1-allyloxycarbonyloxyethyl]-2penem-3-carboxylic acid allyl ester Analogously to Example 1, 1.15 g of 2-[(3S,4R)-3-[(1R)-1-allyloxycarbonyloxyethyl]-4-(4-allyloxycarbonylaminophenoxyacetylthio)-2-oxo-azetidin-1-yl]-2-triphenyllphosphoranylideneacetic acid allyl ester are reacted in 150 ml of toluene to form the title compound.

IR ($CH_2Cl_2$) 3420, 1792, 1735, 1710, 1645 $cm^{-1}$.

The starting material can be manufactured as follows:

a. 4-(allyloxycarbonylamino)-phenoxyacetic acid 0.9 g of 4-aminophenoxyacetic acid is suspended in 15 ml of water, and 2.4 ml of 5N NaOH solution are added. After cooling with ice, 0.63 ml of chloroformic acid allyl ester is added over a period of 5 minutes. After removing the cooling bath, the reaction mixture is stirred for 20 minutes at room temperature. The reaction mixture is then washed twice with ethyl acetate, and the aqueous phase is adjusted to pH 2 with 4N HCl and extracted with ethyl acetate. The organic solution is washed with brine and dried over sodium sulphate. The title compound is obtained after evaporating off the solvent.

TLC (ethyl acetate/acetic acid 95:5) $R_f$=0.4.

b.
2-[(3S,4R)-3-[(1R)-1-allyloxycarbonyloxyethyl]-4-(4-allyloxycarbonylaminophenoxyacetylthio)-2-oxoazetidin-1-yl]-2-triphenylphosphoranylideneacetic acid allyl ester 1 g of 4-(allyloxycarbonylamino)-phenoxyacetic acid is suspended in 2 ml of $CH_2Cl_2$ and 0.6 ml of 1-chloro-1-dimethylamino-2-methylprop-1-ene is added thereto. The mixture is stirred for 75 minutes and is then added dropwise, over a period of 5 minutes, to a solution of 1.74 g of the silver salt of 2-[(3S,4R)-3-[(1R)-1-allyloxycarbonyloxyethyl]-4-mercapto-2-oxo-azetidin-1-yl]-2-triphenylphosphoranylideneacetic acid allyl ester, 50 mg of dimethylaminopyridine and 0.41 ml of pyridine in 30 ml of absolute methylene chloride. The title compound is obtained after working up analogously to Example 1.

IR ($CH_2Cl_2$) 3420, 1755, 1730, 1690 $cm^{-1}$.

Example 7:

The sodium salt of (5R,6S)-2-(4-aminophenoxymethyl)-6-[(1R)-1-hydroxyethyl]-2-penem-3-carboxylic acid.

530 mg of (5R,6S)-2-(4-allyloxycarbonylaminophenoxymethyl)-6-[(1R)-1-allyloxycarbonyloxyethyl]-2-penem-3-carboxylic acid allyl ester are dissolved in 16 ml of absolute THF and, while stirring, 40 mg of tetrakis-triphenylphosphine-palladium and 1.1 ml of tributyltin hydride are added in succession. After 30 minutes, a further 20 mg of tetrakis-triphenylphosphine-palladium and 0.32 ml of tributyltin hydride are added thereto and the whole is stirred for a further 1.5 hours. 15 minutes after the addition of 0.31 ml of acetic acid the reaction mixture is concentrated by evaporation in vacuo and partitioned in water/ethyl acetate. The pH value is adjusted to 7.7 with sodium hydrogen carbonate. After washing twice with ethyl acetate, the aqueous solution is concentrated in vacuo. The pure title compound is obtained by column chromatography on OPTI UPC$_{12}$ (solvent: water). IR (DMSO-d$_6$): 1771, 1616, 1587, 1511 $cm^{-1}$; UV (water): $\lambda_{max}$=302 nm.

Example 8:

(5R,6S)-2-[4-(2-allyloxycarbonylaminoethyl)-phenoxymethyl]-6-[(1R)-1-allyloxycarbonyloxyethyl]-2-penem-3-carboxylic acid allyl ester Analogously to Example 1, 2 g of 2-[(3S,4R)-3-[(1R)-1-allyloxycarbonyloxyethyl]-4-(4-(2-allyloxycarbonylaminoethyl)-phenoxyacetylthio)-2-oxo-azetidin-1-yl]-2-triphenylphosphoranylideneacetic acid allyl ester are converted in 400 ml of absolute toluene into the title compound.

IR (CH$_2$Cl$_2$): 3430, 1790, 1740, 1710, 1640 cm$^{-1}$.

The starting compound can be manufactured as follows:

a. 4-(2-allyloxycarbonylaminoethyl)-phenoxyacetic acid

Analogously to Example 6, 3.9 g of 4-(2-aminoethyl)-phenoxyacetic acid are converted into the title compound.

TLC (ethyl acetate/acetic acid 95:5) R$_f$=0.4.

b. 2-[(3S,4R)-3-[(1R)-1-allyloxycarbonyloxyethyl]-4-(4-(2-allyloxycarbonylaminoethyl)-phenoxyacetylthio)-1-oxo-azetidin-1-yl]-2-triphenylphosphoranylidene-acetic acid allyl ester Analogously to Example 6, 2.25 g of 4-(2-allyloxycarbonylaminoethyl)-phenoxyacetic acid are converted with 3.48 g of the silver salt of 2-[(3S,4R)-3-[(1R)-1-allyloxycarbonyloxyethyl]-4-mercapto-2-oxo-azetidin-1-yl]-2-triphenylphosphoranylideneacetic acid allyl ester into the title compound.

IR (CH$_2$Cl$_2$): 3430, 1750, 1715, 1690 cm$^{-1}$.

Example 9:

(5R,6S)-2-[4-(2-aminoetrhyl)-phenoxymethyl]-6-[(1R)-1-hydroxyethyl]-2-penem-3-carboxylic acid Analogously to Example 7, 0.97 g of (5R,6S)-2-[4(2-allyloxycarbonylaminoethyl)-phenoxymethyl]-6-[(1R)-1-allyloxycarbonyloxyethyl]-2-penem-3-carboxylic acid allyl ester is converted with tributyltin hydride and tetrakis-triphenylphosphine-palladium into the title compound.

IR (DMSO-d$_6$): 1774, 1613, 1585, 1512 cm$^{-1}$;

UV (water): λ$_{max}$=307 nm.

Example 10:

(5R,6S)-2-phenoxymethyl-6-[(1R)-1-allyloxycarbonyloxyethyl]-2-penem-3-carboxylic acid allyl ester Analogously to Example 1, 1.8 g of 2-[(3S,4R)-3-[(1R)-1-allyloxycarbonyloxyethyl]-4-phenoxyacetylthio-2-oxo-azetidin-1-yl]-2-triphenylphosphoranylideneacetic acid allyl ester are converted in 350 ml of toluene into the title compound.

IR (CH$_2$Cl$_2$): 1795, 1750, 1710, 1650, 1600, 1590 cm$^{-1}$.

The starting compound can be manufactured as follows:

Analogously to Example 1, 912 mg of phenoxyacetic acid and 2.61 g of the silver salt of 2-[(3S,4R)-3-[(1R)-1-allyloxycarbonyloxyethyl]-4-mercapto-2-oxo-azetidin-1-yl]-2-triphenylphosphoranylideneacetic acid allyl ester are converted into 2-[(3S,4R)-3-[(1R)-1-allyloxycarbonyloxyethyl]-4-phenoxyacetylthio-2-oxo-azetidin-1-yl]-2-triphenylphosphoranylideneacetic acid allyl ester.

IR (CH$_2$Cl$_2$): 1760, 1690 cm$^{-1}$.

Example 11:

The sodium salt of (5R,6S)-2-phenoxymethyl-6-[(1R)-1-hydroxyethyl]-2-penem-3-carboxylic acid Analogously to Example 4, 654 mg of (5R,6S)-2-phenoxymethyl-6-[(1R)-1-allyloxycarbonyloxyethyl]-2-penem-3-carboxylic acid allyl ester are converted with 230 mg of 1,3-dimethylbarbituric acid and 41 mg of tetrakis-triphenylphosphine-palladium in 12 ml of THF into the title compound.

IR (DMSO-d$_6$): 1771, 1618, 1597, 1492 cm$^{-1}$;

UV (water): λ$_{max}$=307 nm.

Example 12:

Pivaloyloxymethyl-(5R,6S)-2-phenoxymethyl-6-[(1R)-1-hydroxyethyl]-2-penem-3-carboxylate Analogously to Example 5, 103 mg of sodium (5R,6S)-2-phenoxymethyl-6-[(1R)-1-hydroxyethyl]-2-penem-3-carboxylate are converted with 80 μl of iodomethyl pivalate in 2.2 ml of absolute DMF into the title compound.

IR (CH$_2$Cl$_2$): 3600, 1790, 1750, 1725, 1597, 1587 cm$^{-1}$;

UV (ethanol) λ$_{max}$=327 nm.

Example 13:

(5R,6S)-2-[N-(4-allyloxycarbonylaminophenyl)-N-(allyloxycarbonyl)-aminomethyl]-6-[(1R)-1-allyloxycarbonyloxyethyl]-2-penem-3-carboxylic acid allyl ester Analogously to Example 1, 3 g of 2-[(3S,4R)-1-allyloxycarbonyloxyethyl]-4-[N-(4-allyloxycarbonylaminophenyl)-N-(allyloxycarbonyl)-glycylthio]-2-oxo-azetidin-1-yl]-2- 2-triphenylphosphoranylideneacetic acid allyl ester are converted in 500 ml of toluene into the title compound.

IR (CH$_2$Cl$_2$): 3415, 1790, 1730, 1705, 1635, 1595, 1580, 1520 cm$^{-1}$.

The starting compound can be manufactured as follows:

a. N-(4-allyloxycarbonylaminophenyl)-N-(allyloxycarbonyl)glycine

Analogously to Example 6, 3.1 g of N-(4-aminophenyl)-glycine are converted with 4.97 ml of chloroformic acid allyl ester and sodium hydroxide solution into the title compound.

TLC (ethyl acetate/acetic acid 95:5) R$_f$=0.5.

b. 2-[(3S,4R)-3-[(1R)-1-allyloxycarbonyloxyethyl]-4-[N-(4-allyloxycarbonylaminophenyl)-N-(allyloxycarbonyl)-glycylthio]2-oxo-azetidin-1-yl]-2-triphenylphosphoran-ylideneacetic acid allyl ester Analogously to Example 1, 2.67 g of N-(4-allyloxycarbonylaminophenyl)-N-(allyloxycarbonyl)-glycine are converted with 3.5 g of the silver salt of 2-[(3S,4R)-

3-[(1R)-1-allyloxycarbonyloxyethyl]-4-mercapto-2-oxo-azetidin-1-yl]-2-triphenylphosphoranylideneacetic acid allyl ester into the title compound.

IR (CH$_2$Cl$_2$): 3415, 1750, 1740, 1705, 1690, 1520 cm$^{-1}$.

Example 14:

(5R,6S)-2-(4-aminophenylaminomethyl)-6-[(1R)-1-hydroxyethyl]-2-penem-3-carboxylic acid Analogously to Example 2, 315 mg of (5R,6S)-2-[N-(allyloxycarbonylaminophenyl)-N-(allyloxycarbonyl)-aminomethyl]-6-[(1R)-1-allyloxycarbonyloxyethyl]-2-penem-3-carboxylic acid allyl ester are converted with tributyltin hydride and tetrakis-triphenylphosphinepalladium into the title compound.

IR (DMSO-d$_6$): 1767, 1612, 1585, 1517 cm$^{-1}$;
UV (water) $\lambda_{max}$=302 nm.

Example 15:

(5R,6S)-2-[4-(allyloxycarbonylaminomethyl)-2-methoxyphenoxymethyl]-6[(1R)-1-allyloxycarbonyloxyethyl]-2-penem-3-carboxylic acid allyl ester Analogously to Example 1, 2.4 g of 2-[(3S,4R)-3-[(1R)-1-allyloxycarbonyloxyethyl]-4-4-(allyloxycarbonylaminomethyl)-2-methoxyphenoxyacetylthio]-2-oxo-azetidin-1-yl]-2-triphenylphosphoranyl-ideneacetic acid allyl ester are converted in 350 ml of toluene into the title compound.

IR (CH$_2$Cl$_2$): 3440, 1792, 1745, 1720, 1647, 1580, 1510 cm$^{-1}$.

The starting compound can be manufactured as follows:

a. 2-(2-methoxy-4-cyanophenoxy)-acetic acid 0.75 g of vanillic acid nitrile are heated at reflux temperature with 0.94 g of chloroacetic acid and 0.6 g of sodium hydroxide in 3 ml of water. After 20 minutes, the reaction mixture is diluted with 2 ml of water and, after a further hour, 0.2 g of sodium hydroxide in 3 ml of water are added thereto. After a total reaction period of 5 hours, the reaction mixture is cooled and filtered The filtration residue is twice suspended in ethyl acetate and filtered off. The solid material is then taken up in water, and the pH is adjusted to 2 with HCl (4N). After filtering off, the title compound is obtained and is further processed without being purified.

TLC (ethyl acetate/5% acetic acid) R$_f$=0.2.

b. 2-(2-methoxy-4-aminomethylphenoxy)-acetic acid 3.3 g of 2-(2-methoxy-4-cyanophenoxy)-acetic acid are hydrogenated in 90 ml of a 2:1 (by volume) mixture of methanol and 25% aqueous ammonia in the presence of 1.6 g of Raney nickel for 5 hours at room temperature under normal pressure. After filtering off the catalyst, it is washed with methanol and water and the filtrate is then concentrated to dryness. The resulting solid material is triturated with a small amount of water, filtered off and dried over P$_2$O$_5$ in an exsiccator.

c.
2-[4-(allyloxycarbonylaminomethyl)-2-methoxyphenoxy]-acetic acid

Analogously to Example 6, 3.3 g of 2-(4-aminomethyl-2-methoxyphenoxy)-acetic acid are converted into the title compound.

TLC (ethyl acetate/acetic acid 95:5) R$_f$=0.4.

d.
2-[(3S,4R)-3-[(1R)-1-allyloxycarbonyloxyethyl]-4-[4-(allyloxycarbonylamino-methyl)-2-methoxyphenoxyacetylthio]-2-oxo-azetidin-1-yl]-2-triphenylphosphoranylideneacetic acid allyl ester Analogously to Example 1, 2.36 g of 2-[4-(allyloxycarbonylaminomethyl)-2-methoxhyphenoxy]-acetic acid are converted with 3.5 g of the silver salt of 2-[(3S,4R)-3-[(1R)-1-allyloxycarbonyloxyethyl]-4-mercapto-2-oxo-azetidin-1yl]-2-tripphenylphosphoranyl-ideneacetic acid allyl ester into the title compound.

IR (CH$_2$Cl$_2$): 3440, 1755, 1720, 1690 cm$^{-1}$.

Example 16:

(5R,6S)-2-(4-aminomethyl-2-methoxyphenoxymethyl]-6-[(1R)-1-hydroxyethyl]-2-penem-3-carboxylic acid Analogously to Example 2, 910 mg of (5R,6S)-2-[4-(allyloxycarbonylaminomethyl)-2-methoxyphenoxymethyl]-6-[(1R)-1-allyloxycarbonyloxyethyl]-2-penem-3-carboxylic acid allyl ester are converted with tributyltin hydride and tetrakis-triphenylphosphine-palladium into the title compound.

IR (DMSO-d$_6$): 1773, 1614, 1592, 1585, 1517 cm$^{-1}$;
UV (water): $\lambda_{max}$=307 nm.

Example 17:

(5R,6S)-2-(4-formylphenoxymethyl)-6-[(1R)-1-allyloxycarbonyloxyethyl]-2-penem-3-carboxylic acid allyl ester Analogously to Example 1, 0.87 g of 2-[(3S,4R)-3-[(1R)-1-allyloxycarbonyloxyethyl]-4-(4-formylphenoxy-acetylthio)-2-oxo-azetidin-1-yl]-2-triphenyl-phosphoranylideneacetic acid allyl ester is converted in 170 ml of toluene into the title compound.

IR (CH$_2$Cl$_2$): 1797, 1750, 1700, 1650, 1605, 1582 cm$^{-1}$.

The starting compound can be manufactured as follows:

Analogously to Example 6, 1 g of 4-formylphenoxyacetic acid is converted with 2.58 g of the silver salt of 2-[(3S,4R)-3-[(1R)-1-allyloxycarbonyloxyethyl]-4-mercapto-2-oxo-azetidin-1-yl]-2-triphenylphosphoranylideneacetic acid allyl ester into 2-[(3S,4R)-3-[(1R)-1-allyloxycarbonyloxyethyl]-4-(4-formylphenoxyacetyl-thio)-2-oxo-azetidin-1-yl]-2-triphenylphosphoranylideneacetic acid allyl ester.

IR (CH$_2$Cl$_2$): 1760, 1692 cm$^{-1}$.

Example 18:

The sodium salt of (5R,6S)-2-[4-formylphenoxymethyl]-6-[(1R)-1-hydroxyethyl]-2-penem-3-carboxylic Analogously to Example 2, 270 mg of (5R,6S)-2-(4-formylphenoxymethyl)-6-[(1R)-1-ally-loxycarbonyloxyethyl-2-penem-3-carboxylic acid allyl ester are converted with 0.6 ml of tributyltin hydride and 13 mg of tetrakis-triphenylphosphine-palladium in 2 ml of absolute THF into the title compound.

IR (DMSO-d$_6$): 1773, 1684, 1599, 1509 cm$^{-1}$;
UV (water): $\lambda_{max}=283$ nm.

Example 19:

(5R,6S)-2-(4-chloromethylphenoxymethyl)-6-[(1R)-1-allyloxycarbonyloxy-ethyl]-2-penem-3-carboxylic acid allyl ester A solution of 11.2 g of 2-[(3S,4R)-3-[(1R)-1-allyloxycarbonyloxyethyl]-4-(4-chloromethylphenoxyacetylthio)2-oxo-azetidin-1-yl]-2-triphenylphosphoranylideneacetic acid allyl ester in 750 ml of toluene is stirred at reflux temperature under an argon atmosphere for 45 minutes. The solvent is then evaporated off and the crude product is purified by chromatography on silica gel.

IR (CH$_2$Cl$_2$): 1795, 1745, 1710, 1650, 1610, 1590 cm$^{-1}$.

The starting material is manufactured as follows:
2-[(3S,4R)-3-[(1R)-1-allyloxycarbonyloxyethyl]-4-(4-chloromethylphenoxyacetylthio)-2-oxo-azetidin-1-yl]-2-triphenylphosphoranylideneacetic acid allyl ester Analogously to Example 1, 10.8 g of 4-chloromethylphenoxyacetic acid and 23.08 g of the silver salt of 2-[(3S,4R)-3-[(1R)-1-allyloxycarbonyloxyethyl]-4-mercapto-2-oxo-azetidin-1-yl]-2-triphenylphosphoranylideneacetic acid allyl ester are converted into the title compound.

IR (CH$_2$Cl$_2$) 1755, 1690, 1620 cm$^{-1}$.

Example 20:

(5R,6S)-2-[4-(1-methyltetrazol-5-ylthiomethyl)-phenoxymethyl]-6-[(1R)-1-allyloxycarbonyloxyethyl]-2-penem-3-carboxylic acid allyl ester A solution of 400 mg of (5R,6S)-2-(4-chloromethylphenoxymethyl)-6-[(1R)-1-allyloxycarbonyloxyethyl]-2-penem-3-carboxylic acid allyl ester in 2 ml of absolute DMF is cooled to 0° and 0.64 g of pulverised potassium iodide and a solution of 132 mg of sodium 1-methyltetrazole-5-thiolate in 0.8 ml of DMF are added in succession thereto. The reaction mixture is left for 15 minutes at 0° and then for 30 minutes at room temperature. The DMF is then drawn off under a high vacuum and the residue is partitioned between water and ethyl acetate. The organic phase is separated off, washed with brine, dried over sodium sulphate and concentrated. After purification by chromatography on silica gel (eluant toluene/ethyl acetate 92.5:7.5) the pure title compound is obtained.

IR (CH$_2$Cl$_2$): 1795, 1750, 1710, 1650, 1610, 1590 cm$^{-1}$.

Example 21:

The sodium salt of (5R,6S)-2-[4-(1-methyltetrazol-5-ylthiomethyl)-phenoxymethyl]-6-[(1R)-1-hydroxyethyl]-2-penem-3-carboxylic acid Analogously to Example 2, 450 mg of (5R,6S)-2-[4-(1-methyltetrazol-5-ylthiomethyl)-phenoxymethyl]-6-[(1R)-1-allyloxycarbonyloxyethyl]-2-penem-3-carboxylic acid allyl ester are converted with 22 mg of tetrakis-triphenylphosphine-palladium and 122 mg of 1,3-dimethylbarbituric acid in 7 ml of absolute THF into the title compound.

IR (DMSO-d$_6$): 1772, 1617, 1585, 1512 cm$^{-1}$;
UV (H$_2$O): $\lambda_{max}=307$ nm.

Example 22:

(5R,6S)-2-[4-(4-morpholinomethyl)-phenoxymethyl]-6-[(1R)-1-allyloxycarbonyloxyethyl]-2-penem-3-carboxylic acid allyl ester Analogously to Example 20, 0.5 g of (5R,6S)-2-(4-chloromethylphenoxymethyl)-6-[(1R)-1-allyloxycarbonyloxyethyl]-2-penem-3-carboxylic acid allyl ester is converted with 3.3 g of potassium iodide and 105 μl of morpholine in 10 ml of absolute DMF into the title compound.

IR (CH$_2$Cl$_2$): 1790, 1750, 1705, 1650, 1610, 1590 cm$^{-1}$.

Example 23:

The sodium salt of (5R,6S)-2-[4-(4-morpholinomethyl)-phenoxymethyl]-6-[(1R)-1-hydroxyethyl]-2-penem-3-carboxylic acid Analogously to Example 2, 455 mg of (5R,6S)-2-[4(4-morpholinomethyl)-phenoxymethyl]-6-[(1R)-1-allyloxycarbonyloxyethyl]-2-penem-3-carboxylic acid allyl ester are converted with 24 mg of tetrakis-triphenylphosphinepalladium and 131 mg of 1,3-dimethylbarbituric acid in 9 ml of THF into the title compound.

IR (DMSO-d$_6$): 1775, 1612, 1585, 1510 cm$^{-1}$;
UV (water): $\lambda_{max}=307$ nm.

Example 24:

The following compounds are manufactured in a manner analogous to that described in the preceding Examples:

(5R,6S)-2-[3-(aminomethyl)-phenoxymethyl]-6-[(1R)-1-hydroxyethyl]-2-penem-3-carboxylic acid
IR (DMSO-d$_6$): 3435, 2968, 1774, 1616, 1587 cm$^{-1}$;
UV (water): $\lambda_{max}=308$ nm.

(5R,6S)-2-[2-(aminomethyl)-phenoxymethyl]-6-[(1R)-1-hydroxyethyl]-2-penem-3-carboxylic acid
IR (DMSO-d$_6$): 3436, 2968, 1774, 1617, 1585, cm$^{-1}$;
UV (water): $\lambda_{max}=307$ nm.

(5R,6S)-2-[4-(aminomethyl)-phenylaminomethyl]-6-[(1R)1-hydroxyethyl]-2-penem-3-carboxylic acid
UV (water): $\lambda_{max}=308$ nm.

(5R,6S)-2-[4-(aminomethyl)-phenylthiomethyl]-6-[(1R)1-hydroxyethyl]-2-penem-acid
UV (water): $\lambda_{max}=306$ nm. (5R,6S)-2-[2-aminophenoxymethyl]-6-[(1R)-1-hydroxyethyl]-2-penem-3-carboxylic acid
UV (water): $\lambda_{max}=306$ nm.

(5R,6S)-2-[4-(4-aminophenoxy)-phenyl]-6-[(1R)-1-hydroxyethyl]-2-penem-3-carboxylic acid
UV (water): $\lambda_{max}=322$ nm.

(5R,6S)-2-[4-(4-aminomethylphenoxy)-phenyl]-6-[(1R)-1hydroxyethyl]-2-penem-3-carboxylic acid
UV (water): $\lambda_{max}=321$ nm.

(5R,6S)-2-[4-carbamoylphenoxymethyl]-6-[(1R)-1-hydroxyethyl]-2-penem-3-carboxylic acid
UV (water): $\lambda_{max}=300$ nm.

(5R,6S)-2-[2-carbamoylphenoxymethyl]-6-[(1R)-1-hydroxyethyl]-2-penem-3-carboxylic acid
UV (water): $\lambda_{max}=299$ nm;
IR (DMSO-$d_6$): 3453, 1773, 1666, 1620, 1595 cm$^{-1}$.

(5R,6S)-2-[4-(aminomethyleneaminomethyl)-phenoxymethyl]6-[(1R)-1-hydroxyethyl]-2-penem-3-carboxylic acid
UV (water): $\lambda_{max}=307$ nm.

Example 25:

The following compounds are manufactured in a manner analogous to that described in the preceding Examples (process A: see Example 1; process B: see Example 20):

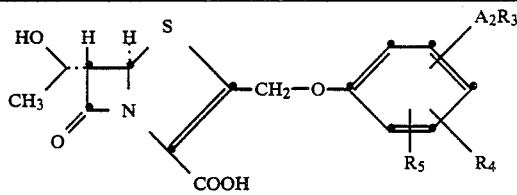

| $A_2-R_3$ | UV (water) $\lambda_{max}$(nm) | IR (DMSO-$d_6$) (cm$^{-1}$) | Process |
|---|---|---|---|
| 4-CH$_2$NHCH$_3$ | 306 | 3435,2968,1773,1615,1586 | A |
| 3-CH$_2$NHCH$_3$ | 305 | | A |
| 2-CH$_2$NHCH$_3$ | 306 | | A |
| 4-CH$_2$NHCH$_2$CH$_2$OH | 307 | | A |
| 3-CH$_2$NHCH$_2$CH$_2$OH | 306 | | A |
| 2-CH$_2$NHCH$_2$CH$_2$OH | 306 | | A |
| 4-CH$_2$NHCH$_2$CH$_2$NH$_2$ | 307 | | A |
| 3-CH$_2$NHCH$_2$CH$_2$NH$_2$ | 305 | | A |
| 2-CH$_2$NHCH$_2$CH$_2$NH$_2$ | 306 | | A |
| 4-CH$_2$NHCH$_2$CH$_2$N(CH$_3$)$_2$ | 306 | | A |
| 4-CH$_2$NHCH$_2$CH$_2$N(morpholino) | 307 | | A |
| 4-CH$_2$NHCH$_2$CH$_2$N(piperidinyl-CONH$_2$) | 308 | | A |
| 4-CH$_2$N(CH$_3$)CH$_2$CONH$_2$ | 306 | | B |
| 4-CH$_2$N(piperidinyl-CONH$_2$) | 305 | 3429,1778,1678,1612,1580 | B |
| 4-CH$_2$N(piperazinyl-NH) | 306 | | B |
| 4-CH$_2$N(piperazinyl-N-CHO) | 305 | 3434,2966,1774,1616,1587 | B |
| 4-CH$_2$N(piperazinyl-N-CH$_3$) | 306 | | B |
| 4-CH$_2$N(piperazinyl-NCONH$_2$) | 306 | | B |
| $R_4, R_5 = 3,4$-O—CH$_2$—O($A_2$—$R_3$ = H) | 311 | | |
| 4-OH ($R_4$ = 3-OH, $R_5$ = H) | 311 | | A |
| 4-OH | 317 | | A |
| 4-OH ($R_4$ = 3-OH, $R_5$ = 5-OH) | 328 | | A |

-continued
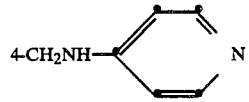
| $A_2-R_3$ | UV (water) $\lambda_{max}$(nm) | IR (DMSO-$d_6$) (cm$^{-1}$) | Process |
|---|---|---|---|
| 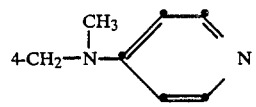 | 308 | | A |
| 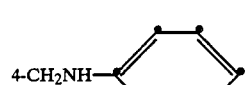 | 308 | | A |
| 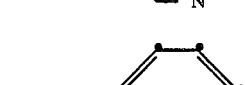 | 307 | | A |
| 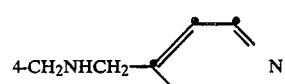 | 309 | | A |
|  | 306 | | A |
|  | 307 | | A |
| 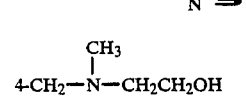 | 306 | | A |
| 4-CH$_2$—N(CH$_3$)—CH$_2$CH$_2$OH | 305 | | B |
| 4-CH$_2$N(CH$_2$CH$_2$OH)$_2$ | 305 | | B |
| 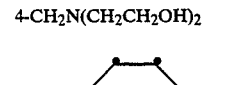 | 305 | | B |
|  | 307 | | B |
|  | 308 | | B |

-continued

[Structure: penem core with HO-CH(CH3)- group, S, N, O=, COOH, =CH-CH2-O-phenyl-A2R3 with R4, R5 on ring]

| A2—R3 | UV (water) $\lambda_{max}$(nm) | IR (DMSO-$d_6$) (cm$^{-1}$) | Process |
|---|---|---|---|
| 4-CH2N [pyridinone with =O, OH] | 310 | | B |
| 4-CH2N [imidazole with N] | 306 | | B |
| 4-CH2—S—[tetrazole with N—N, N, N—CH2—CONH2] | 307 | | B |
| 4-CH2S—[pyridine with N] | 308 | | B |
| 4-CH2—N [cyclohexyl/phenyl with OH, OH] | 306 | | B |
| 4-CH2—N [cyclohexyl/phenyl with OH, OH] | 307 | | B |
| 4-CH2—N [tetrazole with N, N=N] | 306 | | A |

Unless stated otherwise, R4 and R5 represent hydrogen.

Example 26:

The sodium salt of (5R,6S)-2-[4-(dimethylaminomethyl)-phenoxymethyl]-6-[(1R)-1-hydroxyethyl]-2-penem-3-carboxylic acid 70 mg of (5R,6S)-2-[4-(aminomethyl)-phenoxymethyl]-6-[(1R)-1-hydroxyethyl]-2-penem-3-carboxylic acid are dissolved in 7 ml of aqueous tetrahydrofuran. After adjusting the solution to pH 6.81 using 1N HCl, 50 μl of a 37% aqueous formaldehyde solution are added thereto and the whole is stirred for 10 minutes at room temperature under nitrogen (pH~5.9). After adding a mixture consisting of 12.5 mg of sodium cyanoborohydride and 13.75 mg of zinc chloride in 1.5 ml of buffer pH 7, the reaction mixture is adjusted to pH 7.1 with sodium hydrogen carbonate. After stirring for 45 minutes at room temperature, the reaction mixture is concentrated in a rotary evaporator under reduced pressure and the yellow residue is applied in water to a chromatography column. (OPTI UPC$_{12}$; water, then water/acetonitrile 9:1). In this manner, the desired title compound is obtained.

(OPTI UPC$_{12}$; water/acetonitrile 4:1) R$_f$=0.29; UV (H$_2$O): λ$_{max}$=307 nm.

Example 27:

(5R,6S)-2-(4-methoxyphenoxymethyl)-6-(1R)-1-allyloxycarbonyloxyethyl)-2-penem-carboxylic acid allyl ester Following the procedure described in Example 1 2 g of 2-[(3S,4R)-3-[(1R)-1-allyloxycarbonyloxyethyl]-4-(4-methoxyphenoxyacetylthio)-2-oxo-azetidin-1-yl]-2-triphenylphosphoranylideneacetic acid allyl ester is cyclized to the title compound by refluxing in 250 ml toluene.

IR(CH$_2$Cl$_2$); 1795,1750,1710,1590,1510 cm$^{-1}$.

The starting material is prepared as follows: A solution of 2.43 g of the silver salt of 2-[(3S,4R)-3-[(1R)-1-allyloxycarbonyloxyethyl]-4-mercapto-2-oxo-azetidin-1-yl]-2-triphenylphosphoranylideneacetic acid allyl ester in 40 ml of absolute dichloromethane is treated successively with 0.56 ml of pyridine, 20 mg of 4-dimethylaminopyridine and 1.12 g of 4-methoxyphenoxyacetylchloride. The work-up procedure described above gives the desired 2-[(3S,4R)-3-[(1R)-1-allyloxycarbonyloxyethyl]-4-[4-methoxyphenoxymethylthio)-2-oxo-azetidin-1-yl]-2-triphenylphosphoranylideneacetic acid allyl ester.

IR(CH$_2$Cl$_2$);1760,1690,1640 cm$^{-1}$.

Example 28:

The sodium salt of (5R,6S)-2-(4-methoxyphenoxymethyl)-6-[(1R)-1-hydroxyethyl]-2-penem-3-carboxylic acid Following the procedure described in Example 4 0.76 g of (5R,6S)-2-(4-methoxyphenoxymethyl)-6-[(1R)-1-allyloxycarbonyloxyethyl]-2-penem-3-carboxylic acid allyl ester is reacted in 15 ml tetrahydrofurane with 250 mg of 1,3dimethylbarbituric acid and 45 mg of tetrakistriphenylphosphinepalladium to give the title compound. TLC (OPTI UPC$_{12}$; water/acetonitrile 4:1); R$_f$=0.27; IR(DMSO-d$_6$);1772,1618, 1588,1508 cm$^{-1}$; UV (water); λ$_{=312}$ nm.

Example 29:

Dry ampoules or phials, each containing 0.5 g of (5R,6S)-[4-(aminomethyl)-phenoxymethyl]-6-[(1R)-1-hydroxyethyl]-2-3-carboxylic acid as active ingredient, are prepared as follows:

| Composition (for 1 ampoule or phial): | |
|---|---|
| active ingredient | 0.5 g |

| -continued | |
|---|---|
| Composition (for 1 ampoule or phial): | |
| mannitol | 0.5 g |

A sterile aqueous solution of the active ingredient and the mannitol is subjected under aseptic conditions to freeze-drying in 5 ml ampoules or 5 ml phials and the ampoules or phials are sealed and checked.

Instead of the active ingredient mentioned above, it is also possible to use the same amount of another active ingredient from the preceding Examples.

I claim:

1. A compound of the formula

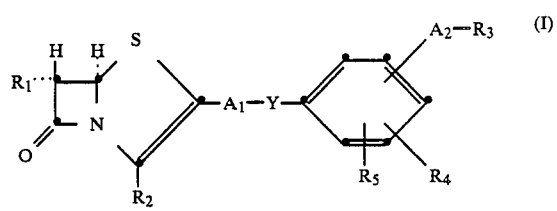

in which R$_1$ is hydroxymethyl or 1-hydroxyethyl, R$_2$ is carboxy or esterfied carboxy that is cleavable under physiological conditions, R$_3$ is hydrogen, amino or amino monoor di-substituted by lower alkyl; lower alkoxy or halogen; each of R$_4$ and R$_5$ represents hydrogen, Y represents a group —O—, A$_1$ is lower alkylene and A$_2$ represents a direct bond or lower alkylene, and pharmaceutically acceptable salts thereof.

2. (5R, 6S)-2-[4-aminomethyl)-phenoxymethyl]-6-[(1R)-1-hydroxyethyl]-2-penem -3-carboxylic acid and pharmaceutically acceptable salts thereof according to claim 1.

3. (5R,6S)-2-[4-(2-aminoethyl)-phenoxymethyl]-6-[(1R)-1-hydroxyethyl]-2-penem-3-carboxylic acid and pharmaceutically acceptable salts thereof according to claim 1.

4. (5R,6S)-2-(4-fluorophenoxymethyl)-6-[(1R)-1-hydroxyethyl]-2-penem-3-carboxylic acid and pharmaceutically acceptable salts thereof according to claim 1.

5. (5R,6S)-2-(4-methoxyphenoxymethyl)-6-[(1R)-1-hydroxyethyl]-2-penem-3-carboxylic acid and pharmaceutically acceptable salts thereof according to claim 1.

6. A method of treating bacterial infections in a mammal comprising administering to said mammal a therapeutically effective amount of a compound according to claim 1 or a pharmaceutically acceptable salt thereof.

7. A pharmaceutical composition comprising an antibacterially effective amount of a compound of the formula I according to claim 1.

8. (5R, 6S)-2-phenoxymethyl-6-[(1R)-1-hydroxyethyl]-2-penem-3-carboxylic acid and pharmaceutically acceptable salts thereof according to claim 1.

* * * * *